United States Patent [19]
Slater et al.

[11] Patent Number: 5,348,636
[45] Date of Patent: Sep. 20, 1994

[54] PROCESSES FOR THE PREPARATION AND SEPARATION OF MACROMOLECULES

[75] Inventors: Gary Slater, Ottowa; Jaan Noolandi, Ontario; Chantal Turmel, Quebec, all of Canada

[73] Assignee: Xerox Corporation, Stamford, Conn.

[21] Appl. No.: 148,239

[22] Filed: Nov. 8, 1993

Related U.S. Application Data

[63] Continuation of Ser. No. 783,967, Oct. 29, 1991, Pat. No. 5,286,434, which is a continuation of Ser. No. 342,261, Apr. 24, 1989, abandoned.

[51] Int. Cl.$^5$ .................... G01N 27/26; G01N 27/447
[52] U.S. Cl. .............................. 204/182.8; 204/299 R
[58] Field of Search .................... 204/299 R, 182.8

[56] References Cited

U.S. PATENT DOCUMENTS 4,830,726  5/1989  Stamato et al. ................ 204/299 R

*Primary Examiner*—John Niebling
*Assistant Examiner*—John S. Starsiak, Jr.
*Attorney, Agent, or Firm*—E. O. Palazzo

[57] ABSTRACT

A process for the electrophoretic separation of charged macromolecules includes applying to the macromolecules a periodic sequence of pulses. Each period comprises a multiplicity of electric field pulses of negative and positive polarities. The negative polarity pulses are applied for a longer total time duration than the positive polarity pulses within each period. The average intensity of the negative polarity pulses is less than the average intensity of the positive polarity pulses.

29 Claims, 3 Drawing Sheets

PROCESSES FOR THE PREPARATION AND SEPARATION OF MACROMOLECULES

This is a continuation of application Ser. No. 783,967, filed Oct. 29, 1991, now U.S. Pat. No. 5,286,434, which is a continuation of U.S. patent application Ser. No. 07/342,261, filed on Apr. 24, 1989 abandoned.

FIELD OF THE INVENTION

The present invention pertains to processes for tile preparation, separation and purification of DNA or other charged macromolecules and, more specifically, to processes for the separation of DNA chromosome fragments.

BACKGROUND OF THE INVENTION

In genetic engineering, DNA is typically studied by severing long DNA chains into smaller fragments using a restriction enzyme. The resulting fragments, which must then be separated according to size or composition, provide the information needed to construct a map or the original DNA chain. Construction of such a map is facilitated by severing the original DNA chain into a relatively small number of long fragments (preferably less than one hundred), as opposed to generating many short fragments; as the number of pieces decreases, it becomes easier to reconstruct the original molecule. Conventional methods of fragment separation are believed to be limited in that mixtures containing fragments with more than 20,000 base pairs cannot be readily or fully separated. Therefore, with conventional methods of separation, the human chromosomes are cut or severed into thousands of fragments to permit the separation thereof, thus reconstruction of the original chain can be extremely difficult.

In an attempt to alleviate many of these difficulties, variations on the standard known electrophoresis method have been developed. For example, U.S. Pat. No. 4,473,452, hereby incorporated by reference, describes a pulsed field gradient gel electrophoresis method, which in one embodiment involves the application of two nonuniform electric fields positioned at approximately right angles to each other as a means separating DNA fragments of over 20,000 base pairs. In addition, according to the Abstract of the '452 patent, there is recited an apparatus for and a method of electrophoretically separating particles by electric fields which are transverse to each other, and alternate between respective high and low intensities out of phase with each other at a frequency related to the mass of the particles, thus permitting movement of the particles in an overall direction transverse to the respective directions of the fields. Also, this patent discloses the use of pulsed and crossed gradient electric fields to separate and resolve DNA fragments of up to several million base pairs.

The '452 patent also discloses that particularly good results are obtained when the switching intervals of the alternate fields are proportional to the mass of the particles to be separated raised to a power of about 1.5. More specifically, this patent illustrates that the proper choice of a frequency at which the change from one field to another should occur is related to the time it takes a particle (molecule) of interest to orient itself into an elongated cylindrical shape, and that this time t is related to the mass of the particle (the molecular weight) M, the effective pore radius of the gel r, and the measured velocity of the particle in the gel v, reference column 6, in accordance with the relationship:

$$t \propto M^{1.5}/(r^2 v)$$

Moreover, in the '452 patent it is indicated that variations such as a differently shaped electrophoresis chamber, or differently produced, distributed or varied electric fields can be used provided that the particles are acted on by electric fields varying with time, permitting them to move in overall directions generally intermediate between at least two of the relevant, operationally significant nonparallel fields. Also, more than two fields can be used providing the net effect is at least to act in the desired manner on a particle first in one direction, then in another direction transverse to the first, thereby moving the particle in a third direction intermediate between the first two. The process of the '452 patent involves the use of crossed alternating inhomogeneous fields to separate large DNA fragments, thereby more complex and costly apparatus is needed, i.e standard electrophoretic equipment cannot be used.

The electrophoretic process disclosed in the '452 patent is also discussed by C. L. Smith and C. R. Cantor in "Pulsed - Field Gel Electrophoresis of Large DNA Molecules", *Nature*, Vol. 319, pages 701 to 702 (1986), and by L. M. Corcoran in "Molecular Karyotypes: Separating Chromosomes on Gels", *BioAssays*, Vol. 3, No. 6, pages 269 to 271 (1985), both of which are hereby incorporated by reference.

Illustrated in U.S. Pat. No. 4,737,251 (WO 87/01955), hereby incorporated by reference, is a method and apparatus for gel electrophoresis employing periodic inversion of the electric field essentially in one dimension, (see Abstract of the Disclosure). Also, according to the Abstract, field inversion gel electrophoresis (FIGE) is used, wherein net migration is achieved by using a longer time, or higher voltage in one direction than in the other direction (see column 2, line 66, to column 3; line 10). Thus, net migration in a given direction can be achieved, for example, by partitioning each switching cycle unequally between the so called forward and reverse directions by imposing a higher voltage in the forward direction than in the reverse direction, and vice versa.

With this process, it is believed that undesirable results, such as the anomalous phenomenon of minimum mobility, are obtained, That is, for example, results where the DNA molecules and the bands they form on an electrophoretic gel during the process do not separate in order of molecular size, preventing quantitative and qualitative analysis of the results because it is not possible to estimate from the results on the gel the size of the molecules separated (see for example FIG. 4 and the description thereof and the working examples, columns 5 to 8).

The '251 patent suggests the use of "switching-interval gradients" (or "ramps") to attempt to reduce the phenomenon of minimum mobility. However, "Ramped Field Inversion Gel Electrophoresis: A Cautionary Note", by T. H. N. Ellis, W. G. Cleary, K. W. G. Burcham and B. A. Bowen, *Nucleic Acids Research*, Vol. 15, Number 13, 1987, page :5489, teaches that the selection of switching-interval gradients does not eliminate the minimum mobility problem for all molecular sizes, such as large molecular sizes, for example, DNA molecules larger than 1,000 kilobase pairs. Also, the aforesaid problem does not allow one to control systematically the process in such a manner that the final position of all the DNA molecules follows a given pattern in the gel.

The '251 patent discloses a method for the separation of DNA fragments containing 15,000 to over 700,000 base pairs by periodically inverting a uniform electric field of a given strength in one dimension. In one embodiment, this process utilizes fields of equal intensities in both directions with the longest pulse duration in the forward direction. In another embodiment, the use of fields of different intensities with equal pulse durations, the forward field being of larger intensity than the reverse field is suggested. Switching- interval gradients are also suggested in the '251 patent. However, this patent does not teach a process to optimize the separation and minimize, or eliminate the phenomenon of minimum mobility. Also, this patent does not suggest how theoretical and experimental results can be selected and used to design systematic separation strategies where one primary objective is to separate the DNA molecules in such a manner to obtain a predetermined band pattern in the gel after electrophoresis, specifically, for example, a linear or logarithmic pattern with a combination of different pulse intensities and/or durations. Furthermore, this patent indicates that switching-interval gradients can be selected to reduce the minimum mobility problem.

In an article by R. G. Snell and R. J. Wilkins entitled "Separation of Chromosomal DNA Molecules from C. albicans by Pulsed Field Gel Electrophoresis", *Nucleic Acids Research*, Vol. 14, No. 11, pages 4401 to 4406 (1986), the authors discuss the method of separation apparently disclosed in the '452 patent. The article indicates that variations in experimental conditions such as pulse time, temperature, and relative voltage conditions have critical effects on the quality of results, and that pulsed field gel electrophoresis can be used to resolve DNA from chromosomes of the Candida albicans and Saccharomyces cerevisiae strains of yeast. According to the aforementioned article, the single most important factor for obtaining optimal resolution was the elevation of the electrophoresis temperature to 35° C. Alteration of relative voltage conditions by 10 percent, pulse time by 20 percent, or temperature by 10 percent was, according to this article, found to destroy the electrophoretic pattern.

"Dependence of the Electrophoretic Mobility of DNA in Gels on Field Intermittency", T. Jamil and L. S. Lerman, *Journal of Biomolecular Structure and Dynamics*, Vol. 2, No. 5, pages 963 to 966 (1985), hereby incorporated by reference, addresses the effect of varying pulse duration and varying the interval between pulses, during which intervals the field is zero depending upon the mobility of DNA fragments in gels. This article illustrates the mobility of lambda DNA fragments containing from 3,400 to 21,800 base pairs when a single pulsed field is applied. The authors concluded that if the interval between pulses remains constant, the apparent mobility increases as the duration of pulses increases, approaching however, a maximum. Additionally, this article discloses that when the pulse duration is constant, the apparent mobility decreases as the interval between pulses becomes longer. This article attributes the changes in apparent mobility due to pulse duration and pulse interval to be relatively small for short fragments of 3,400 base pairs, and quite large for longer fragments of 10,000 base pairs and more. In additions, it is indicated that the dependence of the mobility on pulse interval and duration decreases with decreasing ion concentration in the gel (the authors varied the sodium ion concentration between 0.04 to 0.4M); and these effects become larger with decreasing pore size in agarose. Further, the article presents some mathematical analysis concerning the reasons for the greater effects observed for larger molecules, but provides no quantitative information related to DNA fragments containing more than 22,000 base pairs or to experimental conditions where the field is not zero during the intervals between the main pulses. Also, this article does not appear to mention mathematical analysis as a guide to a process for separating large DNA fragments by choosing optimal experimental conditions for a given mixture of fragments.

In "Prediction of Chain Elongation in the Reptation Theory of DNA Gel Electrophoresis", *Biopolymers*, Vol. 24, No. 12, pages 2181 to 2184 (1985) and "On the Reptation Theory of Gel Electrophoresis", G. W. Slater and J. Noolandi, *Biopolymers*, Vol. 25, No. 3, pages 431 to 454 (1986), both of which are hereby incorporated by reference, there is provided a theoretical discussion of the reptation theory of DNA chain motion with respect to gel electrophoresis. These articles disclose three time scales which can be used to calculate optimal experimental conditions for some of the electrophoretic methods that rely on two or more electric field intensities. They do not, however, for example, provide a full quantitative analysis of the correlation between the time scales, the duration and be intensities of applied field pulses, and the sizes of DNA fragments to be separated for all experimental systems that use pulsed fields.

Many references disclose the basic process of gel electrophoresis. For example, U.S. Pat. No. 3,630,882, hereby incorporated by reference, teaches an apparatus for particle separation wherein a mixture of particles in a suspending medium is subjected to an intermittent DC electrical field of sufficient strength to produce a sharp separation of two or more components of the mixture. The electric field is intermittent or pulsed so that the particles in the material are alternately subjected to high electric field and low or zero electric field.

Also, U.S. Pat. No. 3,870,612 teaches a method of determining the electrophoretic mobility and diffusion coefficient of a macromolecular polymer in solution wherein the macromolecules are driven through the solution by an electric field in a modified electrophoretic cell. The electric field is pulsed, and the pulses are of alternating polarity to allow for the use of high fields and to prevent formation of concentration gradients.

U.S. Pat. No. 4,148,703, hereby incorporated by reference, illustrates a method of electrophoretic purification of electrically charged biomolecules which uses different geometrically shaped electrode configurations, permitting potentially different gradients and enabling different particle velocities, finer separations, and continuous electrophoresis by means of a higher voltage in a smaller area with a decrease in power expenditure. The various electrode systems are alternately turned on and off at a given time independently of one another and for a given duration of time. Also, in U.S. Pat. No. 3,506,554, there is illustrated a process and apparatus for separating electrophoretically active substances, such as proteins. The method utilizes a continuously flowing stream of buffer to transport the substances through a zone having an inert material that is permeable to either the electrophoretically active material or small buffer ions, such as a polyacrylamide gel slab. The process includes applying an electric field first in one direction and then in another direction to enable separation, and the cycle of reversing the direction of the electric field is repeated many times.

There is disclosed in U.S. Pat. No. 4,061,561 an electrophonetic apparatus that allows for high resolution by performing two dimensional migrations in a square tray. The sample selected is subjected to a linear current in one direction, and the tray is then turned exactly 90° so that the first migration is pulled apart from an orthogonal direction. The '561 patent also discloses a multiple-sample applicator that allows an operator to deposit multiple samples on the gel or membrane either simultaneously or one at a time.

A process and apparatus for purifying and concentrating DNA from a crude DNA-containing mixture, such as whole blood, is disclosed in U.S. Pat. No. 4,617,102, hereby incorporated by reference. The apparatus of the '102 patent consists essentially of an agarose gel disc immersed in an electrophoresis buffer solution and supported between two eight-micrometer polycarbonate filters in an electric field. Placing the sample on the disc and applying an electric field results in the separation of the DNA from the other components of the crude mixture. However, the reference does not appear to teach, for example, a method of separating DNA particles of different molecular weights from each other.

Other documents of interest include U.S. Pat. No. 4,322,275; "Fractionation of Large Mammalian DNA Restriction Fragments Using Vertical Pulsed - Field Gradient Gel Electrophoresis", K. Gardiner, W. Laas, and D. Patterson, *Somatic Cell and Molecular Genetics*, Vol. 12, No. 2, pages 185 to 195 (1986); "Mapping of the Class II Region of the Human Major Histocompatibility Complex by Pulsed - Field Gel Electrophoresis", D.A. Hardy et al., *Nature*, Vol. 323, pages 453 to 455 (1986); "New Biased - Reptation Model for Charged Polymers", G. W. Slater and J. Noolandi, *Physical Review Letters*, Vol. 55. No. 15, pages 1579 to 1582 (1985); "Scrambling of Bands in Gel Electrophoresis of DNA", M. Lalande, J. Noolandi, C. Turmel, R. Brousseau, J. Rousseau, G. W. Slater, *Nucleic Acids Research*, Vol. 16, pages 5427 to 5437 (1988); "Pulsed-field Electrophoresis: Application of a Computer Model to the Separation of Large DNA Molecules", M. Lalande, J. Noolandi, C. Turmel, J. Rousseau, G. W. Slater, *Proceedings of the National Academy of Sciences U.S.A.*, Vol. 84, pages 8011 to 8015 (1987).

Further U.S. Patents selected as a result of a general computer search (LEXIS), some of which relate to gel electrophoresis, include U.S. Pat. Nos. 3,948,743; 4,059,501; 4,101,401; 4,181,501; 4,148,703; 4,207,166; 4,244,513; 4,322,225; 4,375,401; 4,391,688; 4,433,299; 4,541,910; 4,545,888; 4,552,640; 4,569,741; 4,608,146; 4,608,147; 4,617,103; 4,631,120; 4,632,743; 4,695,548; 4,707,233; 4,715,943; 4,729,823; 4,740,283; 4,747,918 and 4,794,075.

As a result of a patentability search there were selected U.S. Pat. Nos. 4,441,972; 4,473,452; 4,732,656; 4,737,251 and 4,786,387

U.S. Pat. No. 4,971,671, hereby incorporated by reference, illustrates the combination of known electrophoresis techniques and a new method of correlating the required field pulse characteristics and other process conditions with the size of the fragments to be resolved. Thus, in one embodiment a mixture of DNA particles is deposited in a conventional gel electrophoresis apparatus with a power supply and a single, uniform primary electric field having a positive voltage is applied in pulses in one direction. During the period between primary pulses, a secondary pulse of either a positive or a negative voltage is applied. Alternatively, during the period between primary pulses, secondary "pulses" of zero-field conditions may be applied. The aforementioned mixture of DNA fragments comprises in one embodiment a solution or gel sample containing DNA fragments of at least two different sizes.

For example, a mixture could contain fragments having 100,000; 200,000; 300,000; 400,000; and 500,000 base pairs. The duration of the primary and secondary pulses during the process are selected according to the formulae disclosed by G. W. Slater and J. Noolandi in "On the Reptation Theory of Gel Electrophoresis", *Biopolymers*, vol. 25, pages 431 to 454 (1986), hereby incorporated by reference.

Methods selected for separation of DNA fragments having more than 20,000 base pairs have several disadvantages. In some instances, except for the process as illustrated in the aforementioned '671 patent, commercially available electrophoresis equipment must be modified before these methods can be applied. For example, the process disclosed in the U.S. Pat. No. 4,473,452 patent pertaining to crossed gradient fields, requires extensive alterations to conventional gel electrophoresis apparatus. Also, many of the above described systems intended for separating DNA fragments of more than 20,000 base pairs, except for the process as illustrated in the '671 patent, use relatively high electric fields (above 3 volts/cm) necessitating the implementation of a bulky and expensive cooling system to avoid degradation of the gel and/or the DNA.i

SUMMARY OF THE INVENTION

The present invention provides processes for the separation of charged macromolecules, preferably DNA molecules, using Zero integrated Field Electrophoresis (ZIFE). According to the present invention one can preselect the number or range of molecular sizes of molecules that will be separated. Additionally, the processes obtain large relative: separations between DNA molecules wherein other larger molecules remain at their origin and thus do not interfere with the molecules being separated.

Zero Integrated Field Electrophoresis (ZIFE) minimizes or eliminates the undesirable minimum mobility phenomenon during separation of DNA molecules. The elimination or minimization, of the phenomenon of minimum mobility allows for the design of systematically controlled experiments that provide predictable band patterns on the gel, including DNA molecules with millions of base pairs, with the advantage that these patterns may be selected such that quantitative analysis of the results can be optimized. In addition, Zero Integrated Field Electrophoresis (ZIFE) permits a narrow range of molecular sizes, for example where the smaller and larger molecules in the mixture differ in size by 100 kilobase pairs or less, to be separated with a very large resolution, for example 1 millimeter difference in distance migrated for each kilobasepair difference in size.

In processes for the separation of DNA molecules with Zero Integrated Field Electrophoresis (ZIFE) the pulse conditions (field intensities and pulse durations) are changed frequently during electrophoresis to obtain a linear molecular size versus mobility relationship enabling simple size estimations. The applied electrical field is switched between fields of opposite polarity at regular intervals, and one field, the reverse Field, is applied for a longer duration than the other field.

With Zero Integrated Field Electrophoresis (ZIFE) a periodic sequence of electric field pulses is applied where within each period of the sequence an electric field of one polarity, such as a positive polarity, is applied in one direction, that is the forward direction from the plug where the DNA is initially placed, or in the direction of the net migration of the molecule during the separation, and a second electric field of the opposite polarity and lower intensity, that is a negative polarity is applied in the opposite direction of the first field, that is the inverse or reverse direction, and wherein the second field is applied for a longer duration of time than the first field in each period.

In addition, with Zero Integrated Field Electrophoresis (ZIFE) wherein a periodic sequence of electric field pulses is applied with a period of the sequence comprising a field of one polarity, such as positive polarity of 82 volts applied in one direction, that is the forward direction, and a second field of a lower intensity, such as a negative polarity of −41 volts, applied in the opposite direction of the first field, that is the inverse direction, and wherein the second field is applied for a longer duration of time, that is for example 1.40 times longer than the first field, in each period.

Processes according to the present invention separate DNA fragments of any size including, for example, at least 1 to 10,000) kilobase pairs.

Large DNA fragments are separated without the necessity of using crossed fields. Thus, the present invention provides a method of separating DNA fragments of over 20,000 base pairs with modified conventional, commercially available electrophoresis apparatuses. High resolution can be achieved and/or large molecules be separated in a relatively short time period without the use of an expensive cooling system in most instances.

Furthermore, optimal or preselected resolution of mixtures of DNA fragments can be effected by controlling the experimental parameters of the periodic sequence of electric field pulses during the process. This method of separating mixtures of DNA fragments has reproducible and predictable results.

The method of separating mixtures of DNA fragments wherein low electric fields and specially designed pulse shapes are selected to reduce the broadening of the bands formed by the DNA samples during electrophoresis enables simpler analysis of the results.

In addition, the present invention provides a separation technique that facilitates the analysis of the results by obtaining separations where the relationship between molecular size and mobility is monotonic and generally well behaved. Theory and mathematical analysis can be utilized to estimate the molecular size of unknown fragments, and the optimal process conditions can be estimated from the known upper and lower bounds for the size of the unknown DNA molecules to be separated.

Moreover, the separation of DNA molecules and other charged macromolecules with Zero Integrated Field Electrophoresis (ZIFE), which comprises repeatedly applying to the charged macromolecules a periodic sequence of pulses with each period comprising a multiplicity of electric field pulses of negative and positive polarities. The negative polarity pulses are applied for a longer total time duration than the positive polarity pulses within each period, and the negative polarity pulses are of lower intensities than the positive polarity pulses. Alternately, the average intensity of the negative polarity pulses is less than the average intensity of the positive polarity pulses.

In one embodiment of the present invention the largest electric field may be as low as 1.0 volt/centimeter. Also, with the processes of the present invention, there can be selected a low intensity field in the reverse direction (often as low as 0.3 volt/centimeter), and as the reverse pulses are of a longer time duration than the higher intensity forward pulses the molecules move mostly in low intensity fields, which reduces the tendency of the bands to broaden during electrophoresis, a problem that limits the use of electrophoresis for very large molecules in other pulsed field systems. In addition, the processes of the present invention provide a reliable way of determining in advance the values of the experimental parameters that can be selected to obtain optimal resolution of a given mixture of DNA fragments to assure that the molecules separate in order of molecular size, to enable the assembling of purposeful process control strategies allowing large resolution to be obtained over a narrow range of molecular sizes, or lower resolution to be obtained over a wider range of molecular sizes, and/or to allow simple inter- and extrapolation analysis of the results. Optimal resolution may be referred to as obtaining results wherein all of the fragments of a particular size are located in a distinct band that does not overlap with bands of fragments of another size on the termination of the process.

Also, depending, for example, on the process parameters, DNA separations are accomplished where the molecules separate in order of molecular sizes, where the large molecules, for example 3,000 kilobase pairs or more, do not move and do not interfere with the smaller ones, for example 100 to 1,000 kilobase pairs, and where the mobility versus molecular size relationship is sharp yet monotonic, thus superior control, and accurate analysis of the results can be achieved. For the latter advantages, it is preferred in some embodiments to select computer driven power supplies and/or computer software that analyze the results using previous empirical and/or theoretical results.

For a better understanding of the present invention and its features, experimental data have been presented in tabulated form.

DETAILED DESCRIPTION OF PREFERRED EMBODIMENTS

Figure 1:
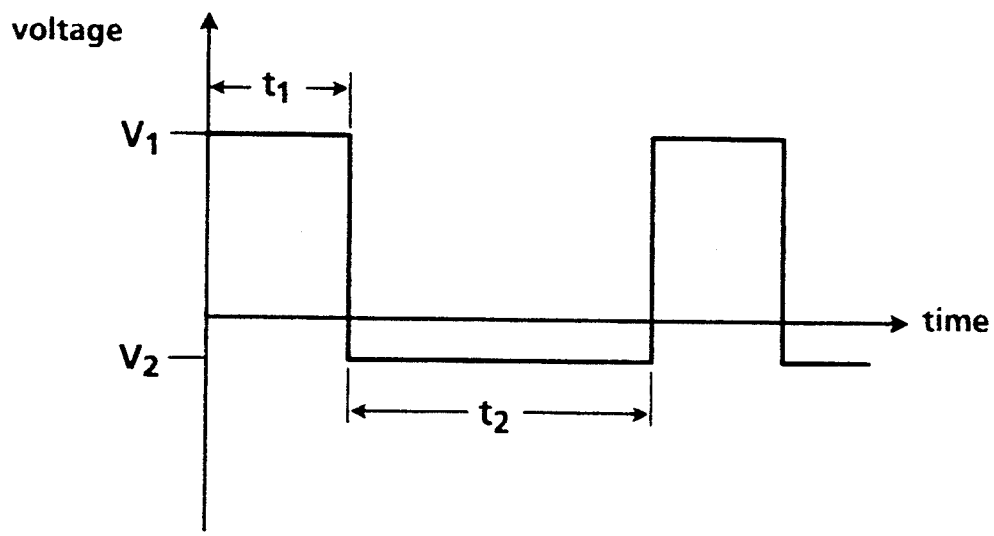
FIG. 1 is a graphical description of a typical pulse shape selected for the process of the present invention in one embodiment; Examples I to X were performed with such a pulse shape.

In one embodiment of the present invention, the process comprises: (1) providing an electrophoresis device; (2) adding to the device a solution mixture or an agarose plug containing DNA fragments of different lengths; (3) energizing the device, thereby creating a periodic sequence of unidirectional uniform electric field pulses therein, said sequence comprising periods within which the field alternates between positive (or forward) voltage pulses, and reverse pulses of a negative polarity and of lesser voltage, on the average, than the forward pulses; (4) estimating the time duration and the field strength required for the forward and reverse field pulses to enable resolution of the fragments into separate and distinct groups (or bands) corresponding to the lengths of the DNA fragments present in each band; (5) applying to the DNA the selected forward and reverse fields with intensities and durations corresponding to the size of fragments to be separated as calculated in step (4), and wherein the reverse field pulses are applied on the average for a longer duration and are of a lower intensity than the forward field pulses. A multiplicity electric fields can also be selected as indicated herein.

A process according to the present invention separates fragments of any desired, or effective size, including for example from 1 to at least 10,000 kilobase pairs. In another embodiment of the present invention, a process is provided which comprises providing a mixture of DNA fragments of desired sizes, depositing the fragments in a conventional known gel electrophoresis apparatus, and applying a periodic sequence of unidirectional field pulses, that is along a single dimension, across the gel, wherein the duration of the electric field pulses in one direction is for a longer period of time that the duration of the electric field pulses in the opposite direction in each period of the sequence, thereby enabling, for example, separation of the fragments according to their sizes. One specific embodiment of the present invention comprises placing a sample of DNA into a gel in an electrophoresis apparatus with a cathode and an anode, applying a periodic sequence of pulses with a period of the sequence comprising a pulse of a first field of one polarity, for example a positive polarity, and a pulse of a field of a second polarity opposite to the first polarity field, for example a negative polarity in this embodiment, wherein the second, or reverse, pulse is applied for a longer duration and is of a lower intensity than the first, or forward, pulse. With the processes of the present invention, zero integrated field gel electrophoresis (ZIFE) can be utilized wherein two fields of opposite polarity and different intensity are selected, and the second or reverse field is of lower intensity and is applied for a longer duration of time than the first field in each period of the periodic sequence. Also, a multiplicity, wherein for example each sequence comprises more than two pulses, of electric field pulses can be selected to form the period of the sequence as indicated herein and wherein the average intensity of the negative polarity pulses is less than the average intensity of the positive polarity pulses.

Advantages associated with the processes of the present invention can include, for example, the elimination, or minimization of the phenomenon of minimum-mobility, where intermediate size molecules migrate slower than both larger and smaller molecules, thus the molecules will migrate in order of molecular size; relative separation between the different DNA species, each of which is forming a band in the gel after the completion of the electrophoresis is usually larger as compared to the separation obtained with other known electrophoresis techniques; optimization of the separation of DNA fragments or molecules enables large relative separations between the DNA molecules wherein, for example, the smaller molecules of 100 kilobase pairs can be directed to move at a much higher speed, for example 20 millimeters per day faster than the larger molecules of a 2,000 kilobase pairs; the direct separation of any desired DNA or polyelectrolyte molecule without first separating other molecules thereby enabling one to determine the order of the molecules being separated; the avoidance of a cooling system or other costly apparatuses to accomplish the rapid electrophoretic separations in most instances; the mobility-molecular size relationship is stepwise and monotonic; the design of systematic separation strategies, where the objective is to separate the DNA molecules in such a manner to obtain a predetermined band pattern in the gel after electrophoresis, specifically, for example, a linear or logarithmic pattern with a combination of different periodic pulse sequences where the pulse intensities and/or durations are changed; a microprocessor can be selected thereby simplifying the control of the process of separation; a simple mathematical analysis of the results where unknown molecular sizes can be estimated from inter- or extrapolations from known results; since low intensity electric fields, may be selected in some embodiments, there is a reduction in the broadening of the bands formed by the DNA samples in the gel during electrophoresis thus increasing the resolution of the process; the pulse shape can be designed specifically to reduce band broadening thus producing electrophoretic separations, for example of DNA molecules, with increased resolution; the separation of very large chromosomes, for example of a size of from about 1,000 to about 6,000 kilobase pairs in a shorter period of time than what is usually the situation with other known electrophoresis techniques; the user can select conditions such that the large molecules in the DNA mixture, for example of size of from about 1,000 to about 6,000 kilobase pairs, will not move during electrophoresis thus rendering the analysis of the final results much simpler; band inversion may be eliminated, or minimized; and the separation of a very large range of molecular sizes, for example molecules between 6 and 6,000 kilobase pairs, on a single gel. With the present invention, different process protocols can be selected and designed, that is the parameters of the periodic sequence of pulses can be modified or controlled during the process, for the primary purpose of providing results, that is determining the position of the DNA molecules on the gel that are simple to analyze and interpret and that optimize the separation between the most relevant DNA molecules for a given biological process embodiment or experiment. For example, one can control the process of the present invention to facilitate the estimation of the size of unknown molecules, such as unknown chromosomes, or to separate a wider range of molecular sizes than is usually obtained with fixed experimental conditions. Examples of modifications of the separation conditions that can be selected to control the process of the present invention and obtain the advantages, or some of the advantages thereof, are as illustrated herein and include an increase or decrease in the field intensities, an increase or decrease in the pulse durations, the selection of a multiplicity of electric fields pulses, which may include pulses of zero-intensity, and the like.

Another embodiment of the present invention is directed to processes for the separation of DNA molecules wherein pulses of fields of opposite polarities are selected for an electrophoresis apparatus, and one of the fields is applied for pulses of a longer duration than the other field. Specifically, one embodiment of the present invention is directed to a process for the separation of DNA molecules with zero field integrated field electrophoresis (ZIFE). A mixture of DNA particles is deposited or placed in a gel electrophoresis device with an anode and a cathode, and a power supply wherein pulses of two electric fields of opposite polarity and of a different intensity are applied to the DNA particles, and wherein the lower intensity electric field (reverse mode) is applied for a longer time duration than the first (higher intensity-forward mode) electric field. The aforementioned DNA fragments comprises a solution, or gel sample containing DNA fragments of at least two different sizes. Thus, for example, a mixture can contain DNA fragments with molecular sizes of 100,000; 200,000; 300,000; 400,000; 500,000 base pairs, and the like fragments. Other molecular sizes not specifically mentioned can be selected providing that the main objectives of, or an objective of, the present invention are achieved.

Processes for the electrophoretic separation of charged macromolecules, including DNA, which comprise applying to the charged macromolecules cycles comprising a multiplicity of electric field pulses of negative and positive polarities, and wherein the negative polarity pulses are applied for a longer total time duration than the positive polarity pulses within each cycle, and the negative polarity pulses are of lower intensities than the positive polarity pulses. In this process embodiment, the cycles are applied for an effective total period of time including, for example, from about 1 to about 10 days. Also, each cycle can comprise, for example, from 2 to about 100 electric field pulses of positive and negative polarities.

Moreover, in a further embodiment of the present invention there is provided a process for the separation of charged macromolecules which comprises continuously applying to the charged macromolecules, such as DNA, cycles containing pulses of a first field and pulses of a second field in an electrophoresis device, and wherein the two fields are of opposite polarity and unidirectional, or along a single dimension, the second field is of lower intensity than the first field, and the second field is applied for a longer duration than the first field for each cycle.

Further embodiments of the present invention include (I) a process for the electrophoretic separation of charged macromolecules which comprises repeatedly applying to the charged macromolecules a periodic sequence of pulses with each period comprising a multiplicity of electric field pulses of negative and positive polarities, and wherein the negative polarity pulses are applied for a longer total time duration than the positive polarity pulses within each period, and the average intensity of the negative polarity pulses is less than the average intensity of the positive polarity pulses; or the negative polarity pulses are of lower intensities than the positive polarity pulses; (11) a process for the separation of a mixture of DNA fragments comprising: (1) providing an electrophoresis device; (2) adding to the device a gel which contains a solution mixture with DNA fragments of different lengths; (3) energizing the device thereby creating a periodic sequence of unidirectional uniform electric field pulses therein, said sequence of field pulses alternating between primary positive voltage pulses and secondary pulses of a negative polarity with less voltage than the primary pulses; (4) estimating the time duration and the field strength required for the primary and secondary field pulses, and the times at which these conditions will be changed during the separation to enable resolution of the fragments into separate and distinct groups corresponding to their lengths with a predetermined relationship between their final location and their sizes; and (5) applying in the device the selected primary and secondary fields with intensities and durations corresponding to the size of fragments to be separated, wherein the second field is applied for a longer duration than the first field in each sequence of pulses; (III) a process for the separation of a mixture of DNA fragments comprising: (1) providing an electrophoresis device; (2) adding to the device a gel which contains a solution mixture with DNA fragments of different lengths; (3) energizing the device thereby creating a periodic sequence of unidirectional uniform electric field pulses therein, said sequence of field pulses comprising a primary positive and a primary negative polarity pulse with the first part of the period comprising a primary positive polarity pulse separated into numerous subpulses by brief secondary pulses of zero intensity and/or negative polarity field, the second part comprising a primary negative polarity pulse separated into numerous subpulses by brief secondary pulses of zero intensity and/or positive polarity field, the primary negative polarity pulses being of lower voltage than the primary positive polarity pulses and the second part of the period being of a longer time duration than the first part; (4) estimating the time duration and the field strength required for the various field pulses to enable resolution of the fragments into separate and distinct groups corresponding to their lengths; and (5) applying in the device the selected sequence of fields with intensities and durations corresponding to the size of fragments to be separated; (IV) a process for the separation of a mixture of DNA fragments or molecules comprising: (1) providing an electrophoresis device; (2) adding to the device a gel which contains a solution mixture with DNA fragments of different lengths or an agarose plug containing DNA fragments of different lengths; (3) energizing the device thereby creating a periodic sequence of unidirectional uniform electric field pulses therein, said sequence of field pulses alternating between primary positive voltage pulses and secondary pulses of a negative polarity with less voltage than the primary pulses; (4) estimating the time duration and the field strength for the primary and secondary field pulses, and estimating the times at which said conditions will be changed during the separation to enable resolution of the fragments into separate and distinct groups corresponding to their lengths with a predetermined relationship between their final location and their sizes; and (5) applying in the device the selected primary and secondary fields with intensities and durations corresponding to the size of fragments to be separated, wherein the second field is applied for a longer duration than the first field in each sequence of pulses; and (V) a process for the separation of a mixture of DNA fragments or molecules comprising: (1) providing a known electrophoresis device; (2) adding to the device a gel which contains a solution mixture with DNA fragments of different lengths or an agarose plug containing DNA fragments of different lengths; (3) energizing the device thereby creating a periodic sequence of unidirectional uniform electric field pulses therein, said sequence of field pulses comprising a primary positive and a primary negative polarity pulse with the first part of the period comprising a primary positive polarity pulse separated into numerous subpulses by brief secondary pulses of zero- intensity and/or negative polarity field, the second part comprising a primary negative polarity pulse separated into numerous subpulses by brief secondary pulses of zero- intensity and/or positive polarity field, the primary negative polarity pulses being of lower voltage than the primary positive polarity pulses and the second part of the period being of a longer time duration than the first part; (4) estimating the time duration and the field strength for the various field pulses to enable resolution of the fragments into separate and distinct groups corresponding to their lengths; and (5) applying in the device the selected sequence of fields with intensities and durations corresponding to the size of fragments to be separated.

The present invention includes a process for the separation of a mixture of DNA fragments comprising: (1) providing an electrophoresis device; (2) adding to the device a gel which contains a solution mixture with DNA fragments of different lengths; (3) energizing the device, thereby creating a sequence of unidirectional uniform electric field pulses therein, said sequence of field pulses alternating between primary positive voltage pulses, which define the direction of net migration in the gel, and secondary pulses of a negative polarity with less voltage than the primary pulses; (4) estimating the time duration and the field strength required for the primary and secondary field pulses to enable resolution of the fragments into separate and distinct groups corresponding to their lengths; (5) applying in the device the selected primary and secondary fields with intensities and durations corresponding to the size of fragments to be separated, wherein the second field is applied for a longer duration than the first field. With the aforementioned process, and other process embodiments illustrated herein, there can also be selected a multiplicity of electric field pulses within each cycle.

In a further specific embodiment of the present invention, a multiplicity of electric field pulses of a positive polarity of intensities between 0 and about +10 volts/centimeter, and of durations between 0.1 and 10,000 seconds, and a multiplicity of electric field pulses of negative polarity of intensities between 0 and about 10 volts/centimeter (at least one pulse has to have a non-zero positive intensity and one a non-zero negative intensity) and wherein the reverse pulses are of a longer total time duration than the positive polarity pulses, can be selected and applied along a single dimension of the gel; and wherein the positive polarity defines the net direction of the migration. This series of pulses, which is repeated for a period of 1 to 10 days, may be applied to an agarose gel with a concentration of 0.4 to 2 percent (weight percent) containing the macromolecules such as DNA. Also, one may modify the field(s) and/or the pulse duration(s) as appropriate, especially to achieve the elimination or minimization of minimum mobility, for example every 2 to 48 hours with a switching device. Also, a computer program can be written to drive the aforesaid modifications automatically or the user can change the conditions manually at regular intervals, for example about every 6 hours. No cooling system is usually selected in most instances as the voltages selected, typically between 20 and 200 volts in commercially available gel boxes or electrophoresis devices, for many of the process embodiments of the present invention are not normally heating the system to a large extent.

When the separation is completed, the gel is removed from the electrophoresis apparatus and a dye is added, normally ethidium bromide, which dye sticks to the DNA and can be seen and traced with UV light. A photograph of the gel can then be taken by a UV sensitive camera. The photograph indicates where the DNA has migrated during the process, and this information can be used to determine the size of unknown molecules or to study qualitatively the genome reorganizations of an organism. The aforementioned dye addition and photograph sequence is applicable to all the process embodiments of the present invention, however, other methods may be selected for the visualization of the DNA. One can also use the DNA separated as samples for further biology experiments by cutting out the DNA bands in the gel before UV light is used. Also, one can select radioactive labeled DNA probes to identify the DNA molecules or chromosomes separated by the process of the present invention.

In another specific embodiment of the present invention a forward field of +1 to about a + (positive) 10 volts/centimeter for pulses of duration between 0.1 and about 10,000 seconds, and a reverse field of −0.25 to about a negative −10 volts/centimeter for pulses of duration between 1.1 and 3 times longer than the forward pulses can be selected. This series of pulses may be applied to an agarose gel having a concentration of 0.4 to 2 percent for a period of 1 to about 10 days. Also, one may change the field(s) and/or the pulse duration(s) as appropriate to achieve, for example, the elimination or minimization of minimum mobility, for example every 2 to 48 hours with a switching device. Further, a computer program can be written to accomplish these and other ZIFE process modifications automatically or the user can change the conditions manually at regular intervals, for example about every 6 hours. When the separation is completed, the gel is removed from the electrophoresis apparatus and a dye such as ethidium bromide can be added thereto as indicated herein. A photograph of the gel is then taken by a UV sensitive camera. The photograph indicates where the DNA has migrated during the process, and this information can be used to determine the size of unknown molecules or to study qualitatively the genome reorganizations of an organism. One can also use the DNA separated by this process embodiment as samples for further biology experiments by cutting out the DNA bands in the gel before UV light is used. Also, one can select radioactive labeled DNA probes to identify the DNA molecules or chromosomes separated by this process embodiment, or other process embodiments of the present invention.

Although it is not desired to be limited by theory, the following equations are provided to primarily enable one to optimize the processes of the present invention and to determine experimental conditions, including, for example, the preferred process parameters in some embodiments. Thus, for example, optimal separation is predicted to occur for a ZIFE configuration as illustrated herein, that is the process of the present invention, and not for the prior art FIGE processes. The ZIFE process of the present invention is based in one aspect on the mobility of macromolecules, such as DNA, which mobilities are in continuous fields, a function of the electric field (in the relevant range of field intensities), for example DNA gel electrophoresis is a nonlinear phenomenon in an agarose gel:

▶ $\mu \propto E\beta$ with $0 \leq \beta \leq 2$

This relationship has been observed experimentally and explained by the biased reptation model of DNA gel electrophoresis, see for example "Quantitative Analysis of the Three Regimes of DNA Electrophoresis in Agarose Gels", by G. W. Slater, J. Rousseau, J. Noolandi. C. Turmel, M. Lalande (1988), *Biopolymers* 27,509 to 524, which is directed to continuous field electrophoresis, hereby incorporated by reference.

The mobility of DNA is proportional to the orientation of the molecule in the field direction, see for example "The Biased Reptation Model of DNA Gel Electrophoresis", by G. W. Slater, J. Noolandi (1989) in *New Trends in Physics and Physical Chemistry of Polymers*, ed. by S. Lee (Plenum Press), to be published, hereby incorporated by reference. When the orientation is negligible, for example when the molecular conformation is isotropic, the exponent $\beta$ is of order zero, and one has a linear regime where molecules can be separated in continuous fields; this usually happens only for relatively small molecules in low electric fields, typically below 20,000 base pairs in size. When the orientation is large, for example the molecule is aligned along the field axis, the nonlinear regime $1<\beta\leq 2$ is reached and continuous field electrophoresis generally fails to separate large molecules, a disadvantage avoided with the ZIFE processes of the present invention as illustrated herein. Thus, for the processes of the present invention, when the field is changed from $E_1$ to $-E_2$, the orientation of the molecular conformation consumes a certain time, $\tau<^*$, before it adapts to the new field. During a time $t<\tau^*$ immediately after the field is changed, the conformation of a large DNA molecule remains oriented as if it were still in a field $E_1$, and thus the mobility remains essentially unchanged and is equal to ▶ $\mu_1 \propto (E_1)\beta$ for $t<\tau^*$ If the field $E_1$ is applied for a pulse duration $t_1$, followed by an $E_2$ pulse of duration $t_2<\tau^*$, the net velocity of a large DNA molecule is thus ▶ $V^0 = [t_1\mu_1 E_1 - t_2\mu_1 E_2]/[t_1+t_2]$ for $t_{1,2}<\tau^*$ and $\mu_1 E_1 > \mu_2 E_2$ After a time $t>\tau^*$ subsequent to changing the field, the conformation is completely adapted to the new field intensity and direction, and it does not have any memory of the previous field conditions. With this limit, the net electrophoretic velocity is given by:

▶ $V_\infty = [t_1\mu_1 E_1 - t_2\mu_2 E_2]/[t_1+t_2]$ for $t_{1,2}>\tau^*$ and $\mu_1 E_1 > \mu_2 E_2$ With the time and field ratios $RE=E1/E2$ and $Rt=t1/t2$, these asymptotic velocities can be written as:

▶ $V_0 = \mu_1 E_1 [R_t - 1/R_E]/[R_t+1]$ $V_{28} = \mu_1 E_1 [R_t - (R_E)-\beta-1]/[R_t+1]$ where all absolute values but one (the velocity $\mu_1 E_1$) are replaced by relative values (ratios). The ratio $R_V$ and the difference $\Delta V$ between these velocities are ▶ $R_V = V_{28}/V_0 = [R_t R_E - (R_E)-\beta]/[R_t R_E - 1]$ ▶ $\Delta V = V_{28} - V_0 = \mu_1 E_1 (R_E)^{-1}[1-(R_E)^{-\beta}]/[R_t+1]$ The ratio $R_V$ and the differential velocity $\Delta V$ are measures of the separation power of the process and, therefore, are usually at a maximum for the optimal use of the ZIFE processes of the present invention. With regard to $V_0=0$ for $R_E=1/Rt$, these equations indicate that the high frequency ($t_{1,2}<\tau^*$) velocity V0 of the DNA molecules is zero if the field ratio is the inverse of the time ratio ($R_E=1/Rt$), which means that no minimum mobility can then usually occur among the large molecules, which would be very useful in situations where normal FIGE conditions, see "Electrophoretic Separations of Large DNA Molecules by Periodic Inversion of the Electric Field", by G. F. Carle, M. Frank, M. V. Olson (1986) *Science* 232, 65 to 68, fail to separate molecules in order of molecular size. In the above ZIFE situation, the net integrated value of the field (neither of the two fields are equal to about zero) during one complete cycle (or period) is about zero:

▶ $\int E\, dt = t_1 E_1 - t_2 E_2 = t_1 E_1 [R_t R_E - 1] = 0$

This condition can be referred to as Zero- Integrated Field Electrophoresis, or ZIFE. When this occurs, the ratio RV becomes infinite since the two fields are of different intensities ($R_E>1$):

▶ $R_V = R_V(R_E = 1/R_t) = [1 - (R_E) - \beta]/0 \to \text{infinity}$

The separation $\Delta V$ is large under these conditions for a ratio $RE \approx 1.5$ to 3, thus the time ratio is $R_t \approx 0.3$ to 0.7. With the processes of the present invention, numbers of the aforementioned order have been selected in some embodiments. The use of $R_E>1$ and $R_t>1$ has been suggested, see "Pulsed Field Electrophoresis: Application of a Computer Model to the Separation of Large DNA Molecules", by M. Lalande, J. Noolandi, C. Turmel, J. Rouseau, G. W. Slater (1988), *Proc. Natl. Acad. Sci. U.S.A.* 84, 8011 to 8015, hereby incorporated by reference. With the process illustrated in this article, however, minimum mobility effects, limited resolution, large band broadening, and other disadvantages resulted. With the processes of the present invention and based primarily on experimental evidence it is believed that the most optimal conditions for DNA separation is found for $R_E>1$ and $R_t<1$, with $R_E \approx 1/R_t$.

Electrophoretic separation of DNAs of different molecular sizes occurs under the aforesaid ZIFE conditions because the critical time $\tau^*$, which can be theoretically calculated or estimated from experimental results, is a function of the molecular size. As a first approximation ▶ $\tau^* \propto M_Y E^{-\delta}$ The exponents $\gamma$ and $\delta$ (both are positive) can be obtained from experimental results or theory, see for example: "The Biased Reptation Model of DNA Gel Electrophoresis", by G. W. Slater, J. Noolandi (1989) in New Trends in Physics and Physical Chemistry of Polymers, ed. by S. Lee (Plenum Press), to be published, the disclosure of which is totally incorporated herein by reference. From this relationship, one can define a critical molecular size $M^*$ such that $t_2 = \tau^*(M^*)$. For a given choice of experimental conditions, that is for example with fixed fields and pulse durations, all molecules with a molecular size $M<M^*$ will have a velocity $V \approx V_{28}$, while all molecules with a molecular size $M>M^*$ will have a (much lower) velocity $V \approx V_0 \approx 0$.

With the present invention, $M>M^*$ molecules actually have near-zero velocities, while the smaller $M<M^*$ molecules retain a finite velocity $V_\infty$ that can be optimized. Therefore, the relative separation $RV = V_{28}/V0$ is extremely large, substantially greater than 1, and the differential velocity $\Delta V$ can be a large fraction of the continuous field velocity $\mu_1 E_1$. The molecules with $M \approx M^*$ have a very strongly" size-dependent velocity and can, therefore, be separated over a wide range of velocities $0 \approx V_0 \leq V \leq V_{28}$.

The ZIFE configuration processes of the present invention can lead to very small asymptotic velocities $V_\infty$ in several embodiments. Preferably, values of $R_t$ slightly larger than $1/R_E$ (the theoretical value for optimum results) are selected to obtain absolute separations and optimum process times. These preferred values do not change the qualitative characteristics of the ZIFE processes, and thus the above equations continue to be applicable. Although the total integrated field is approximately equal to zero, the approach can be referred to as ZIFE. Therefore, in general, ZIFE is a process where $R_E > 1$ (reverse field is of lower intensity than the forward field), and $1/R_E \leq R_t < 1$ (reverse pulse duration larger than forward pulse duration) thus rendering the ZIFE processes of the present invention substantially different than the prior art FIGE process. The results presented in the following Examples also evidence considerable improvement (for example, wider range of molecular sizes separated, no minimum mobility, the larger molecules have zero-velocity) as compared to the prior art FIGE processes (where $R_E$ and $R_t < 1$, or $R_E > 1$ and $R_t = 1$), and where these and other advantages illustrated herein are not believed to be present.

One of the main advantages of the ZIFE process of the present invention over other pulsed field electrophoresis systems, such as FIGE, is that the present process evidences no or little minimum mobility effect since the velocity versus pulse duration relationship is nearly stepwise for a given molecular size M as follows $$V(t_2 < \tau^*(M)) \approx 0; \; V(t_2 > \tau^*(M)) \approx V_\infty$$

that is for example larger molecules MM* remain stationary during the separation process.

Also, the relative separation $R_V$ and the differential velocity $\Delta V$ between two different fragments can be made very large by selecting the appropriate experimental conditions as indicated herein. Further, the process of the present invention can be used to separate a very narrow range of molecular sizes centered around $M \approx M^*$ when the process is accomplished with a single set of experimental conditions (fields E 1 and E2, and pulse durations $t_1$ and $t_2$). Also, the ZIFE process provides for the design of theory- and/or experimental-based process controls, where experimental conditions are varied frequently during an electrophoretic separation. This process control can be designed in a manner that the experimental results will follow any desired pattern in the gel subsequent to completion of the process; which occurs, for example, in view of the monotonic and sharp molecular size versus mobility relationship provided by the ZIFE process. For example, one can impose a linear or logarithmic velocity versus molecular size relationship by designing an appropriate process control which could improve the accuracy of the size estimations obtained with the processes of the present invention. Since the two (or more) fields are applied along a single direction, the processes of the present invention avoid the need for a new electrophoresis gel system, rather there can be selected commercially available conventional electrophoresis devices with a power supply, for example a microcomputer that modulates the DC field provided by a DC power supply that delivers the ZIFE pulses. Furthermore, since the lower field $E_2$ is applied for a longer period of time, its intensity can be selected such that little or no heat is generated during the reverse pulses; even if the forward field $E_1$ is large enough to generate heat, the system can cool down during the longer $t_2$ pulses, and a cooling system is usually unnecessary. Also, since the molecule bands tend to broaden in large electric fields, the use of low intensity field $E_2$ for the longer pulses also reduces the band broadening compared to other known techniques, including FIGE.

Therefore, the ZIFE process provides, for example, very large separations (for example $R_V > 1$), and the monotonic mobility-size relationships (where there is no minimum mobility effect) allows the flexibility not believed to be provided by other known prior art processes. The simplicity of the apparatus, the possibility to accomplish accurate quantitative size estimates and the possibility to systematically control the process to meet special requirements are among the advantages that the ZIFE process of the present invention provides. Although the above ZIFE process equations are presented for only two pulses, a multiplicity of pulses providing the total integrated field of these pulses is about zero, and the like can be selected as indicated herein.

The examples that follow and the other information provided herein evidence that the ZIFE processes of the present invention possess many of the advantages illustrated herein. Table I, Examples I to IX, evidences how the electrophoretic velocity $V(t_1)$ varies with t1 (in seconds) for a situation where $R_t = 1/1.40$, which satisfies the condition $1/R_E \leq R_t < 1$ in all situations, and the molecular sizes varied from about 6 to 6,000 kilobase pairs (kbp). The migration for Examples 1 to IX was for a period of 65 hours and the migrated distances for the various fragments were measured in millimeters from the photographs of the gel as indicated herein. Zones of very large resolution are marked by stars (xx). The results evidence that in the range from about 6 to 6,000 kbp, the ZIFE process of the present invention can improve the separation of DNA molecules without concern for the undesirable phenomenon of minimum mobility which is avoided or minimized with the process of the present invention; for example, in any given column of Table I, that is for any given experiment, the distance migrated by the molecules decreases for larger molecules without intermediate size molecules having migrated over much smaller distances than both larger and smaller molecules. The optimal separation conditions marked by stars on this table also indicate what conditions could be part of a process control strategy when, for example, a wide range of molecular sizes are to be separated on a single gel.

The process of the present invention can be used for the separation of DNA fragments of varying sizes without resorting to crossed-field gel electrophoresis and its accompanying complications. Also, the present invention eliminates the need to accomplish numerous preliminary experiments to determine the optimal separation conditions, especially since ideal parameters can be provided as part of the process. In addition, the present invention can be used to separate mixtures of fragments of any size as indicated herein. Theoretically, the sizes of fragments to be separated are unlimited; generally, however, fragments ranging in size of from about 2,000 base pairs to 6,000,000 base pairs can be resolved with the process of the present invention. Furthermore, the process of the present invention can be selected to obtain reproducible results permitting DNA fragments of a given size to be separated by the same sequence of field pulses in different commercially available gel electrophoresis cells when all other process conditions are retained. Moreover, with the present process research will be facilitated in areas such as separation of chromosomal DNA, chromosomal mapping, production of genetic libraries, and studies on the effects of various drugs on chromosomal DNA.

The electrophoresis device that may be selected for use in the present invention includes a standard gel electrophoresis cell of the type commonly available commercially, such as the Model H1 available from Bethesda Research Laboratories Life Technologies Inc. (P.O. Box 6009, Gaithersburg, Md. 20877) or the Model H3 available from the same company. These devices generally contain an anode, a cathode, and a gel bed. Also, the dimensions of the Model H1 are 47×22×12.5 centimeters; the gel bed is 25×20 centimeters; the distance between the electrodes is 41 centimeters; and the platinum electrodes (0.25 millimeter diameter) are 19 centimeters across the gel bed. The device or box can be constructed of plexiglass and contains 2.5 liters of buffer solution. The dimensions of the Model H3 are 37×12.8×6.5 centimeters; the gel bed is 14×11 centimeters; the distance between the electrodes is 31 centimeters; and the platinum electrodes (0.25 millimeter diameter) are 9.5 centimeters across the gel bed. The gel bed is constructed of plexiglass and contains 0.9 liter of buffer solution. The two electrodes may be comprised of any noncorrosive metal, although platinum wire is preferred.

A solution mixture or an agarose plug containing DNA fragments is placed in the gel bed of the device. One solution selected contains a gel comprising a weak agarose solution containing at least 0.2 percent by weight of agarose dissolved in a buffer at high temperature (about 100° C.) and maintained at 60° C. until the gelation takes place. The concentration of agarose should usually be at least 0.2 percent, and normally no more than 2 percent, with the preferred values being between 0.8 and 1.4 percent in this embodiment. A preferred gel is Agarose NA, a high purity grade gel available from Pharmacia AB, Molecular Biology Division, Uppsala, Sweden. The gel may have a thickness of 0.2 to 2 centimeters with the preferred value being around 0.5 centimeter. The buffer comprises a solution of 0.089M tris base (Trizma base, Sigma Chemical Company, St. Louis, Mo.), 0.089M boric acid, and 0.002M EDTA (ethylenedinitrolo tetraacetic acid disodium salt), however, other similar or equivalent buffers may be selected.

The DNA fragments may be obtained from any source. Examples of DNA fragments separated with the processes of the present invention include intact genomes from bacteriophages (N4, T2, T5, Aeh-II, G, Charon21-a), yeasts strains (Saccharomyces Cerevisia YP148 and S. Pombe 2476), and restriction fragments of human and mouse DNA (in size range from about 1 to about 3000 kilobase pairs). The yeast strain YP148 with 100 to 2400 kbp DNA fragments were obtained from the Institut de Recherches en Biotechnologie, 6100 Avenue Royalmount, Montreal, Quebec, Canada H4P 2R2. The yeast S. Pombe 2476 was obtained from American Type Culture Collection, 12301 Parklawn Drive, Rockville, Md. 20852. The bacteriophages N4, Aeh-II and G were obtained from H. W. Ackerman, Departement de Microbiologie, Universite Laval, Quebec, Canada G1K 7P4. The bacteriophages T2 and T5 were obtained from the Departement de Microbiologie, Universite de Montreal, Montreal, Canada. The small fragments which were obtained from Bethesda Research Laboratories Life Technologies, Inc. consist of λ-DNA/HIND-III fragments ranging in size from 2.0 to 23.1 kilobases (catalogue no. 5612SA).

The DNA fragments may be loaded into the gel in liquid samples or in agarose plug samples. Usually, the liquid samples are selected for fragments smaller than 170 kilobasepairs (λ-DNA/HIND-III fragments, and N4, T2, T5 bacteriophage genomes). The yeasts samples were prepared by procedures based on the technique described by C. R. Cantor and D.C. Schwartz in *Cell*, Vol. 37, pages 67–75 (1984), the disclosure of which is totally incorporated herein by reference. The human, mouse, and Aeh-II and G phase DNAs were prepared by a modified version of the technique described by K. Gardiner, W. Laas, and D. Patterson in *Somatic Cell and Molecular Genetics*, Vol. 12, No. 2, pages 185 to 195 (1986), the disclosure of which is totally incorporated herein by reference.

The electric field that energizes the gel electrophoresis device can be generated by various suitable power supplies. The timed power supply for low- voltage electrophoresis was designed as a self-contained direct current power supply capable of supplying 100 milliamps current at voltages between 0 and +100 volts. This power supply can be driven by a microcomputer which runs software that enables the user to select the ZIFE conditions illustrated herein.

The duration of the applied field pulses is chosen, for example, according to the size of the molecules to be separated and to the type of separation necessary for the biology. Other factors to be considered are the buffer component and concentration, temperature, pore size (or agarose concentration), field strength, and the like. The electric fields as indicated herein may be applied for pulses of about one tenth of a second to about 10,000 seconds, and the reverse pulses are applied for a longer period of time on the average.

The electric field pulses are not limited to any particular shape. By shape is meant, for example, the rapidity or graduality with which the voltage increases with respect to time when a pulse is applied or terminated. A plot of voltage versus time illustrates the concept of field shape. For example, a square field pulse is one wherein the voltage increases immediately to the value determined to be optimal, and remains at that value for the entire duration of the pulse. A voltage versus time plot for such a field appears in FIG. 1.

FIG. 1 represents the voltage versus time plot of a square field pulse as used in Examples I to X. Voltage may range between about +10 and about −10 volts/centimeter. Time may range between about 0.1 and about 10,000 seconds for the pulses, and the reverse pulse is applied for a longer period of time (t). In Examples I to X, the reverse pulses were of longer duration, with $t_2/t_1 = 1.40$. The total integrated field over one complete cycle is about zero.

Other pulse shapes that satisfy the condition that the total integrated field is about zero are also acceptable. For example, the square pulse may contain very short periods of zero or reverse voltages, which assists in the desirable reduction of band broadening, reference FIG. 2, which illustrates schematically the pulse shape selected for Example XI.

Figure 2:
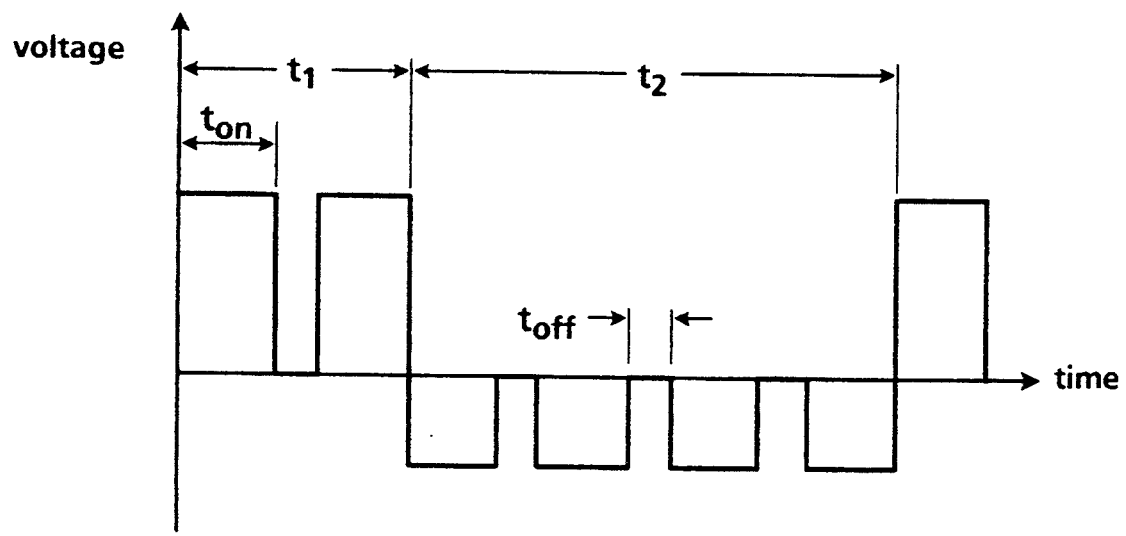
FIG. 2 represents an alternative pulse shape to that shown in FIG. 1 that was used for Example XI.

FIG. 2 represents the schematic pulse shape for the ZIFE process of Example XI. The forward and reverse pulses (of durations $t_1$ and $t_2$, respectively) were divided in numerous duration parts ton separated each by a short period of time toff where the field was zero. This short relaxation period reduced the broadening of the bands formed by the megabase DNA molecules, and also contributed to the cooling of the system. The field could also be reversed or simply reduced during the periods $t_{off}$.

The field shape is not limited to those described; many other shapes are possible. The shape of the field may be selected for each separation to be performed in order to optimize separation of the fragments. A field of a particular shape may better match the microscopic stretching and relaxation processes responsible for a particular DNA separation than would other field shapes.

Fragment separation is determined, for example, in terms of how far each group of fragments of a given size has travelled during the period in which the electric field was applied. Dye markers of ethidium can be selected as indicated herein to stain the entire gel. The gel is then illuminated with ultraviolet light, and the images are recorded by an ultraviolet sensitive camera (UV transilluminator), using a 550 nanometers long-pass filter, available from Ultraviolet Products, Inc., San Gabriel, Calif. Alternatively, a Joyce-Lobel densitometer Chromoscan 3 model can be used to trace the bands in the gel.

A computer program for facilitating the DNA gel electrophoresis process of the present invention can be selected as indicated herein. This program would allow for continuous recalculation of the optimal experimental parameters as the experiment or process progresses. In addition, such a program may provide a rapid means of performing the ZIFE calculations, and also may provide another means of identifying the groups of fragments separated on termination of the process.

A program can be created or written that allows the user thereof to accomplish the following:
1. the selection of pulse shape, pulse durations and intensities, process duration, and when the pulse conditions should change, reference Example XI, and/or
2. the selection of tables containing previous experimental results and/or theoretical equations to select or calculate the optimal experimental conditions (process control parameters including pulse shapes, durations and intensities, duration of the process, number and importance of each pulse condition) automatically, given the molecular sizes and the type of separation desired. This program may also select in combination tables of previous experimental results together with extrapolation protocols obtained from theory. By using standard experimental conditions, such as temperature, buffer and agarose concentration, the program renders the analysis of the final results simpler and the computer program self-learning.

It is believed that the ZIFE processes illustrated herein can be used more efficiently by selecting a computer program to drive the power supply according to the ZIFE process of DNA gel electrophoresis.

Experimental conditions suitable for the ZIFE process can also be changed by a mechanical switch or other similar simple devices.

Also, it is believed that the processes of the present invention can be used in some embodiments, reference Example X, more efficiently by selecting a computer program that can control the power supply according to the ZIFE process of DNA gel electrophoresis in a manner that the final result evidences a linear relationship between the mobility and the molecular size over a preselected range of molecular sizes. Alternatively, this program can also drive the power supply according to the ZIFE process of DNA gel electrophoresis in a manner that the final result evidences instead a logarithmic (or any other relationship for that purpose) relationship between the mobility and the molecular size over a preselected range of molecular size. This program would be useful in one preferred embodiment of the present invention.

The following working Examples are illustrative in nature and are not intended to limit the scope of the invention in any way. Other equivalent methods of practicing the present invention may occur to those skilled in the art.

EXAMPLES

To provide flexibility for pulsed field gel electrophoresis of the present invention, a system has been developed and utilized that provides programmable control of the fields applied to the gels while monitoring some of the conditions induced by these applied fields. The system consists of a microprocessor running the MS-DOS operating system for basic processor control parameters and a specially written program, GELPHOR, see FIG. 4, to generate the field control functions and record some of the operating conditions.

HARDWARE

The machine used was a generic version of the IBM-XT configured with 640 Kb memory, floppy disk drive, 20 Mb fixed disk, high resolution graphic display card, serial and parallel ports, clock, high resolution monochrome monitor and a dot matrix printer.

The hardware utilizes A/D and D/A boards supplied by Strawberry Tree Inc. to implement the control and monitoring process. Probes are supplied to monitor the temperature and field in the solution and a low value resistor is included in the circuit of the gel controller to monitor current flow.

Figure 4:
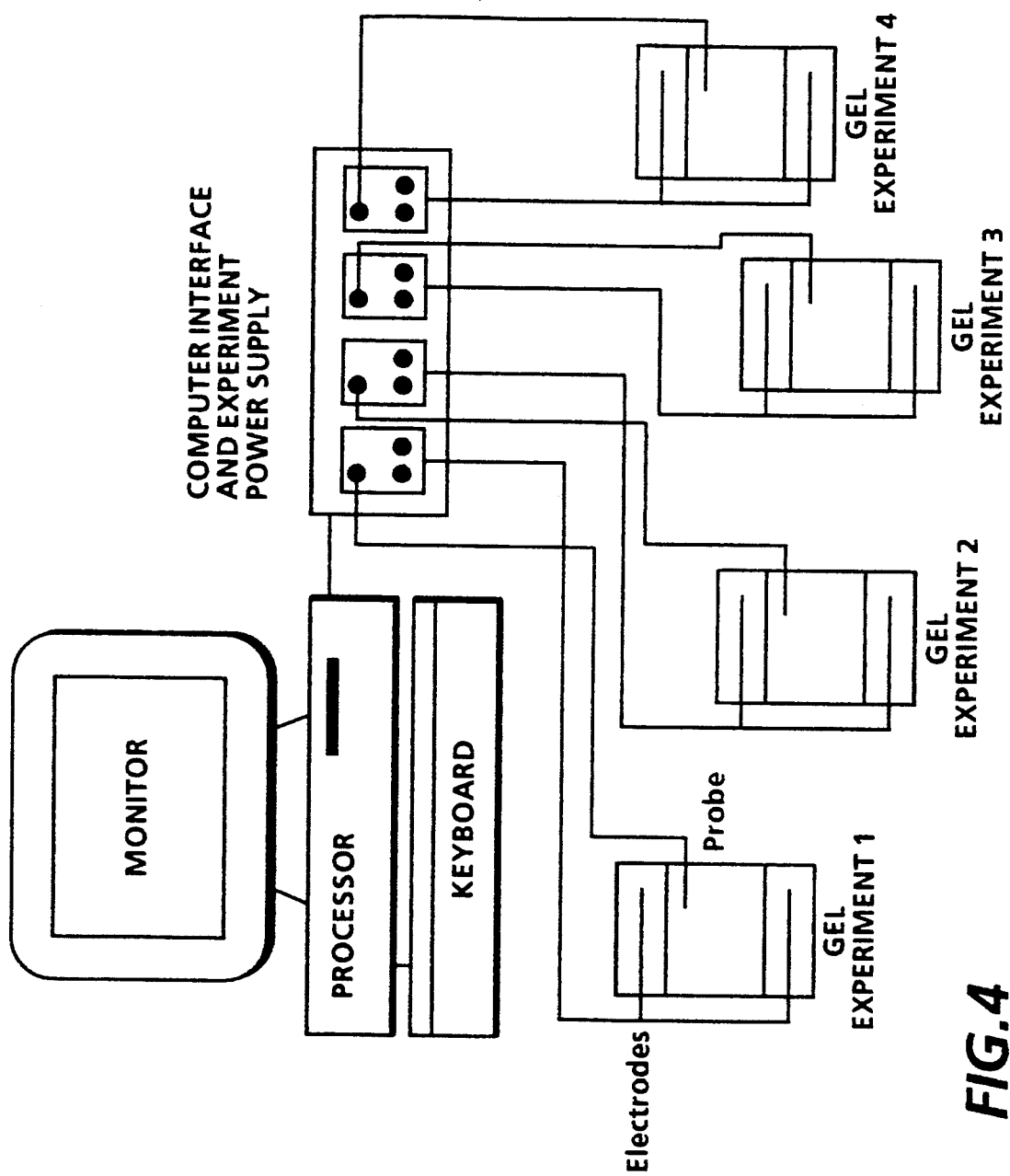
FIG. 4 shows a layout of a gel electrophoresis control system including computer interface and experiment power supply.

The controller was the power supply for the gel trays and the signal conditioner for the measurements. The unit is capable of supplying power to four trays, that is four electrophoresis devices, however, for Example XI the H3 electrophoresis gel device (Gel Experiment 1) or one tray was selected with a maximum current of 0.1 Amps at 90 volts (direct current) in both the positive and negative directions. Signals are received from gel probes, and translated to suitable values for returning to the analog to digital convertor board. This board is capable of monitoring sixteen channels to an accuracy of twelve binary bits (1 part in 4096). FIG. 4 illustrates schematically the equipment set up to control the four trays.

The probes are comprised of a plexiglass housing containing two platinum electrodes to measure the voltage drop in the electrolyte and a glass encased platinumresistance element to monitor the temperature rise under the chosen pulse conditions. The method used to insert the probe into the gel was to drill a ⅜ inch diameter hole in the gel box cover at the extremity of the gel closest to the negative (black) voltage terminal.

SOFTWARE

Program Gelphor

The methods and displays of the Program Gelphor are partly based on a set of functional specifications. This program allows one to run different experiments on four separate trays simultaneously. Setting up each experiment was a simple process in which the program itself will guide the user through. First, we define a PULSE and how it is described to the program.

A pulse is a periodic sequence of voltages defined over ode cycle as a series of duration times (in seconds) and the voltage to be applied to the tray electrodes for that duration. For example, if it is desired to apply a simple square wave alternating between +50 volts and −50 volts every 30 seconds (for Example XI, V1 was 82 volts, and V2 was −26 volts; and the times were as recited in Example XI), it would be specified as the list 30 50 30-50. The first 30 is the duration time for which 50 volts is to be applied, the second 30 the duration for which −50 volts is to be applied. The program will repeat this sequence over and over for a length of time specified as indicated herein.

Both time and voltage can be decimal numbers. Each number must be separated from the others by one or more spaces. There is no specific limit to the number of duration-voltage pairs one cad select to specify a pulse (subject to the finite size of computer memory), but pulses with hundreds of duration-voltage pairs are feasible. A saw-tooth pulse with the voltage changing every tenth of a second could be described as follows: 0.1 0 0.1 5 0.1 10 0.1 15 0.1 20. This is interpreted as a tenth of a second at 0 volts, a tenth at 5 volts, a tenth at 10 volts and so on. These two examples illustrate all the duration times being the same, however, they can be of any value from 0.01 second up, for example up to about one year.

Program Gelphor provides up to 10 distinct pulses to each of the electrophoresis trays in a timed sequence that the user describes.

Figure 5:
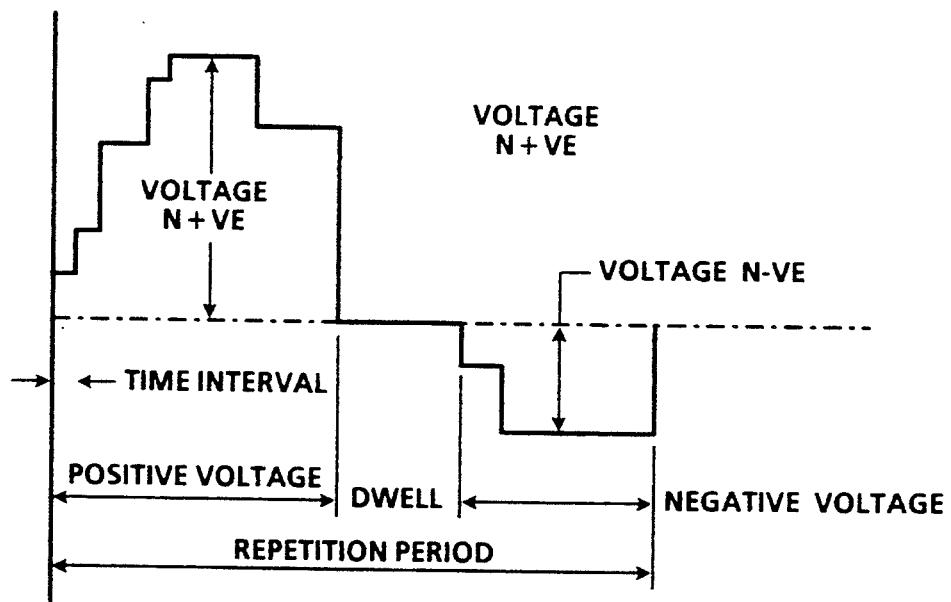
FIG. 5 shows a pulse profile typical for a computer program which can be used to run the present invention.

Individual pulse descriptions are stored on named files which contain lists of time voltage pairs as text characters in exactly the format described in the previous paragraph. Making such a file manually is simple (program Gelphor contains facilities to guide the user through the process), however, complex pulse shapes, which were not utilized for Example XI can be generated by another program based on theoretical predictions. Pulse files can have any name, but must conform to the Disk Operating System (DOS) format, which is a name up to 8 characters long followed by a period and then a 3 character extension. Gelphor will only recognize files with the extension PLS (short for pulse), thus one can, for example, identify the square pulse as indicated herein, SQUARE.PLS, and the saw-tooth SAW.PLS. A representation of a pulse profile is illustrated in FIG. 5. When one creates pulses through the programs facilities, it is not necessary to type in this extension, it will be added automatically when the files are stored on disc.

EXAMPLES I TO X

Eighteen different DNA molecules obtained from λ/Hind-III (the fragments of 6.6, 9.4, 23.1 kilobase pairs), from a digest of the p80 plasmid C-fps/fes by the EcoRI restriction enzyme, American Type Culture Collection, (the fragment of 14 kbp), from the Charon 21-a phage C41.7 kbp), from the T5 and T2 phages (125 and 170 kbp, respectively), from the Aeh-II phage (230 kbp), from the yeast YP-148 (360,460, 540,700, 1,600 and 2,400 kbp), and from the G-phage (700 kbp) and from the yeast S. Pombe (3,000, 4,500 and 6,000 kbp) was selected for a series of nine Examples to illustrate the wide range of applicability and the high resolution power (the separation between two molecules of DNA that are close in size is large enough to enable their identification) of the ZIFE process of the present invention. Samples of each of the above 18 DNA molecules in amounts of about 100 nanograms per molecule were placed in each of the 9 gels, 0.8 percent agarose gel in a buffer comprising a solution of 0.089M tris base, 0.089M boric acid, and 0.002M EDTA, and these samples were added to a Model H3 or a Model H1 electrophoresis device, both available from Bethesda Research Laboratories Life Technologies, Inc., which devices contained a cathode and an anode. The temperature of the device was not controlled by any cooling system, and remained around 25° C. for all the Examples. Also, the time ratio was fixed at $1/R_t = 1.40$, and the fields were varied between 2.67 and 0.7 volt/centimeter with the field ratio being in the range of $R_E = 2.0$ to 2.5. For the application of the above electric field, there were selected as the two power supplies two Model GPF 200/400, available from Pharmacia LKB, which power supplies were connected to a Model H Intervalometer, available from Sound Scientific, Seattle, Wash. The Model H Intervalometer enables switching between the two fields, $V_1$, $V_2$, of the pulsed sequence as follows.

A voltage of $+V_1$ was applied in the forward direction between the electrodes of the H 1 and H3 devices in square shape pulses (FIG. 1) of t1 seconds, and a voltage of $-V_2$ in square shape pulses (FIG. 1) was applied in the reverse direction for $t_2$ seconds between the $V_1$ pulses. This periodic sequence was repeated for a total time duration of 65 hours. Thereafter, the power supply was discontinued. A total of nine gels were removed from the H1 and H3 devices. There thus resulted nine gels with separated DNA molecules therein, which gels were then individually stained with ethidium bromide dye markers (0.5 microgram per milliliter of buffer). The gels were then illuminated with ultraviolet light and the locations of the DNA fragment bands were recorded by an ultraviolet sensitive camera (UV transilluminator) using a 550 nanometers long-pass filter. The results thereof are presented in Table I (IA, IB and IC), Examples I to IX.

The first column in the tables, DNA Size (in kbp) provides the molecular size of the DNA molecules selected. The other 9 columns provide the distance migrated (location) in millimeters for each of these DNA molecules. $V_1$ and $V_2$ refer to the voltages applied between the two electrodes in the electrophoresis device indicated, H3 or H1, and $t_1$ and $t_2$ refer to the pulse duration time. The stars ** indicate the range of molecular sizes for the Examples which provided the highest resolution. Thus, the highest resolution for Example I was between 41.7 and 71 kbp.

In Table I, the 102 mm (millimeters) was the distance traveled by the 6.6 kilobase pairs of DNA molecule (see the first column for size) under the experimental conditions described in the heading of column two (which can be read in the space directly above the 102 mm). Similarly, the distance travelled by the other molecules in the different experiments can be read from this Table.

The number between stars (xx) in Table I as indicated herein illustrates for each Example the range of molecular sizes where the maximum separation, or resolution, was obtained. As evidenced by the results presented in this Table, changing the pulse duration and/or the voltages enables one to select the range of molecular sizes where the separation (or resolution) is maximum. Also, there is no or little minimum mobility effect, that is in each column the larger molecules were migrating at a slower speed than the smaller ones, except in those situations where the distance migrated was about zero, or slightly more, see Example II, 4 mm, 1 mm, 1 mm, and the 3 mm's, thus rendering the small minimum mobility effect of substantially no consequence.

Other similar examples of separation can be accomplished by varying the gel, the buffer, the temperature, the molecular sizes of the DNA, $V_1$, $V_2$, $t_1$, $t_2$, and the like; and further the number of pulses in each cycle (or the period of the periodic sequence of field pulses) can be more than two as indicated herein.

Further, a computer program was written based, for example, primarily on the results of Table I, and other information presented herein, which computer program specifically determines the process control strategy including, for example, the pulse duration to be selected, and the electric field intensities to be utilized to separate, for example, a wide range of molecular sizes on the same gel. In Example X that follows, logarithmic separation was achieved in this manner.

EXAMPLE X

The process of Example I was repeated with the exceptions that the two pulse durations $t_1$, $t_2$ were changed manually 6 times as indicated in Table II during the process. Table II that follows provides the pulse durations values of $t_1$ and $t_2$ for each of the six periodic sequences of square shaped pulses selected for the 65 hours, and the fraction (in percent) of the 65 hours where each of these periodic sequences were selected. Pulse durations (first column) and fraction of the total experimental duration (second column) are shown for the process described in Example X.

These conditions were selected with a simple computer algorithm to achieve a logarithmic relationship between DNA molecular size and mobility (that is mobility $\propto$ log(molecular size)) on completion of the 65 hour experiment for DNA molecules in the molecular size range 23 to 2,400 kilobase pairs. The percentages in Table II were calculated by a computer algorithm, see Appendix I, the disclosure of which is totally incorporated herein by reference, using results from systematic experiments, including the data presented in Table I, Examples I to IV, and Table III. Experimental data used to calculate the percentages are the same as in Table II. In the first column, DNA size (in kbp) provides the molecular size of the DNA molecules selected. The other two columns provide the distance migrated in millimeters by each of these DNA molecules in the 23 to 2,400 kbp range during the experiments, whose pulse conditions are given in the top row. The results of this ZIFE electrophoretic separation are shown in FIG. 3.

Figure 3:
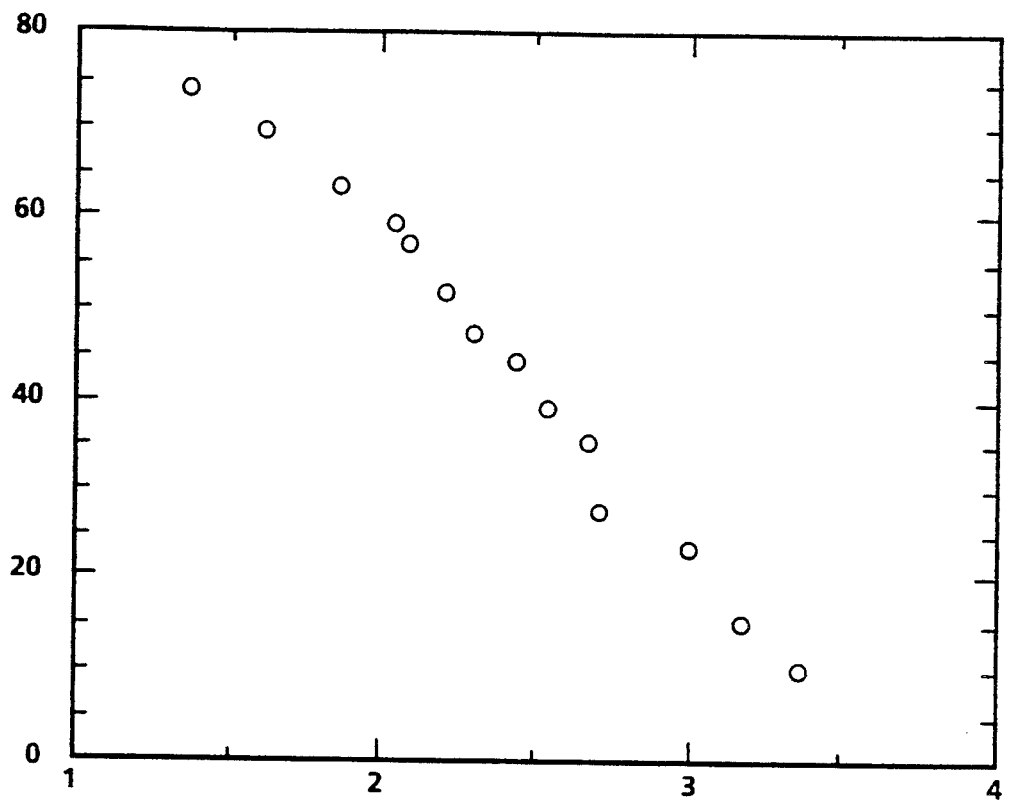
FIG. 3 provides the experimental results in terms of the distance traveled (in millimeters per 65 hours of migration) in the gel by each group of DNA fragments (logarithm of molecular sizes on the x-axis) present in the initial mixture for Example X; Table II provides the experimental parameters for controlling this process.

In FIG. 3 there are provided the results of the ZIFE process of Example X where the pulse durations were selected according to Table II. The y-axis provides the distance migrated by the DNA molecules whose sizes are provided on the x-axis in terms of the logarithm (base 10) of their size in kilobase pairs. The points fall approximately on a straight line, indicating that the process control described in Table II yields a logarithmic separation over that range of molecular sizes, thus permitting size estimation of unknown DNA molecules.

As indicated herein, the y-axis provides the position of the molecules on the gel on completion of the process (as measured in millimeters from the original position at time zero), while the x-axis provides the logarithm of molecular size (in kilobase pairs) of the DNA molecules used in the experiment. For example, the first point (the highest one) indicates that the 23.1 kilobase pairs molecule (read $\log_{10}(23.1) = 1.36$ on the x-axis) has migrated over a distance of 74 millimeters (read this distance from the y-axis) during the 65 hour experiment.

The points fall approximately on a straight line indicating a logarithmic relationship between molecular size and mobility:

$$\mu = a + b \times \log_{10}(M)$$

where a and b are constants, $\log_{10}(M)$ is the logarithm of molecular size (in kilobase pairs) of the DNA molecules, and $\mu$ the mobility of the latter. Such a relationship allows the separation of a wide range of molecular sizes on a single gel (here 23 to 2,400 kbp molecules were separated in a single experiment), and facilitates the size estimation of unknown DNA molecules by interpolation. Also, no minimum mobility effect occurs, that is no two molecules have the same mobility, reference FIG. 3.

Other process control protocols can be designed easily by those skilled in the art for other purposes, for example to separate molecules in other size ranges or to have linear mobility versus molecular size relationships.

EXAMPLE XI

The process of Example I was repeated with the following exceptions. The pulse conditions were $t_1 = 300$ seconds, $t_2 = 420$ seconds, $V_1 = 82$ volts and $V_2 = -26$ volts. The distance between the electrodes in the H3 gel box was 31 centimeters, and the fields were $E1 = 265$ volts/centimeter and $E_2 = -0.83$ volts/centimeter. The S. Pombe chromosomes (approximate molecular sizes 3,000, 4,500, 6,000 kilobase pairs) were electrophoresed with the pulse shape shown on FIG. 1 and also with the pulse shape shown on FIG. 2 with $t_{on} = 1$ second and $t_{off} = 0.25$ second. These pulse sequences were applied to the gels with a PC driven power supply, see Appendix II attached hereto, the disclosure of which is totally incorporated herein by reference.

Where the pulse shape corresponds to FIG. 1, all the DNA was in a large band (or smear) located between the origin and a distance approximately equal to 15 millimeters on the gel. Where the pulse shape corresponds to FIG. 2, that is wherein brief periods (0.25 second) of zero-field intensity were inserted within the long electric field pulses, three bands formed at distances 5, 12 and 18 millimeters with widths the order of 2.5 millimeters each. The insertion of the aforementioned zero-field periods of duration, toff, within both parts of the ZIFE cycle, as shown schematically on FIG. 2, enabled bands narrow enough to be identifiable on the photographs. The above process conditions with brief periods of zero-field intensity with the preferred pulse shape of FIG. 2 allows the separation of megabase molecules of 3,000, 4,500, and 6,000 kilobase pairs in about 3 days without excessive band broadening, thus each band did not overlap with the next ones.

With further respect to the processes of the present invention, the meaning of the terms and phrases pulses, multiplicity, periodic sequence, intensity average intensity, period, and the like are well known to those familiar with the subject matter illustrated herein. However, the following information concerning these terms and phrases is provided without being desired to be limited thereby. Periodic sequence of pulses refers to a group of consecutive electric field pulses, for example from about 2 to 100 pulses, that is repeated for an extended time duration, for example from about 1 to about 100 hours. Each pulse has its own intensity, polarity and duration, and the sequence contains two or more different pulses. After the entire sequence has been applied, it is repeated (periodic). After a sequence has been repeated many times or for an extended time duration, it may be changed for a different sequence, which will contain another set of pulses, and which also can be repeated many times or for an extended time duration. The period of the sequence refers to, the total time taken to complete the sequence of pulses. Multiplicity of electric field pulses indicates that each sequence may comprise two or more pulses; and negative and positive field polarities indicates that each pulse has a field polarity. The positive polarity refers to the direction of the net migration of the DNA or other molecules in the gel, while the negative polarity refers to the opposite direction, that is it refers to the opposite direction of the net migration of the DNA or other molecules in the gel. Each sequence or period contains at least one positive and one negative polarity pulse. The average field intensity of a pulse sequence refers to the field intensity that would provide an equal DNA migration in the absence of a gel; for a sequence of pulses, it is computed as the sum of the products of the pulse intensities multiplied by the pulse durations, divided by the sum of the pulse durations, considering only the nonzero intensity pulses of the sequence; the zero intensity pulses can be present, however, they need not be selected for the average field calculations. In ZIFE, the processes of the present invention, the average field intensity in the forward direction is larger than the average field intensity in the reverse direction; however, since the reverse pulses are applied for a longer time duration, the average field intensity over a complete period is about zero. While not being desired to be limited to theory, it is believed that any pulse shape that possesses these characteristics can be selected to separate DNA or other similar molecules in a gel.

With specific reference to the calculation of the average field intensities, the following nonlimiting examples are provided:

1) Situation where one positive and one negative polarity pulse within each period are present. If the positive polarity pulse is of field intensity of +2 volts/centimeter and of a duration of 20 seconds, while the negative polarity pulse is of a field intensity of −1 volt/centimeter and of a duration of 40 seconds, the average positive polarity field intensity is +2 volts/centimeter, and the average negative polarity field intensity is −1 volt/centimeter. The overall average field intensity is then $$[(+2)\times(20)+(-1)\times(40)]/(20+40)=0$$
volts/centimeter where the numerator contains the sum of the products field multiplied by the duration, and the denominator contains the sum of the durations only as described above.

2) Situation where two positive and two negative polarity pulses within each period are present when the pulses are:
   +4 volts/centimeter for 20 seconds
   +3 volts/centimeter for 30 seconds
   −2 volts/centimeter for 40 seconds
   −1 volt/centimeter for 90 seconds.

The average positive polarity field intensity is then:
$[(+4)\times(20)+(+3)\times(30)]/[20+30]=+17/5$ volts/centimeter$=+3.4$ volts/centimeter.

The average negative polarity field intensity is then:
$[(-2)\times(40)+(-1)\times(90)]/[40+90]=-17/13$ volts/centimeter$=-1.31$ volts/centimeter.

The average overall field intensity is then:
$[(+4)\times(20)+(+3)\times(30)+(-2)\times(40)+(-1)\times(90)]/[20+30+40+90]=0$ volts/centimeter.

The negative polarity pulses are applied for a longer total time duration than the positive polarity pulses refers to the sum of the time durations of the negative polarity pulses as being larger or greater than the sum of the time durations of the positive polarity pulses. The zero-field intensity pulses can usually be of any duration when present.

Other modifications of the present invention may occur to those skilled in the art based upon a reading of the present disclosure; these modifications are intended to be included within the scope of the present invention.

TABLE I

| DNA Size (in kbp) | EXAMPLE I<br>$V_1 = 82$ volts<br>$V_2 = -41$ volts<br>$t_1 = 2$ sec.<br>$t_2 = 2.8$ sec.<br>H3 gel box | EXAMPLE II<br>$V_1 = 82$ volts<br>$V_2 = -41$ volts<br>$t_1 = 5$ sec.<br>$t_2 = 7$ sec.<br>H3 gel box | EXAMPLE III<br>$V_1 = 82$ volts<br>$V_2 = -41$ volts<br>$t_1 = 10$ sec.<br>$t_2 = 14$ sec.<br>H3 gel box |
|---|---|---|---|
| 6.6 kbp | 102 mm | 84 mm | 93 mm |
| 9.4 kbp | 93 mm | 78 mm | 88 mm |
| 14.0 kbp | — | — | — |
| 23.1 kbp | 68 mm | 62 mm | 73 mm |
| 41.7 kbp | 50 mm | 54 mm | 68 mm |
| 71 kbp | 22 mm | 41 mm | 61 mm |
| 125 kbp | 10 mm | 19 mm | 47 mm |
| 170 kbp | 11 mm | 4 mm | 23 mm |
| 230 kbp | — | 1 mm | 4 mm |
| 360 kbp | — | 1 mm | 1 mm |
| 460 kbp | — | 3 mm | 1 mm |
| 540 kbp | — | 3 mm | 1 mm |
| 700 kbp | — | 3 mm | 1 mm |
| 1600 kbp | — | 3 mm | 1 mm |
| 2400 kbp | — | 3 mm | 1 mm |
| 3000 kbp | — | 3 mm | 1 mm |
| 4500 kbp | — | 3 mm | 1 mm |
| 6000 kbp | — | 3 mm | 1 mm |
| DNA Size (in kbp) | EXAMPLE IV<br>$V_1 = 82$ volts<br>$V_2 = -41$ volts<br>$t_1 = 30$ sec.<br>$t_2 = 42$ sec.<br>H3 gel box | EXAMPLE V<br>$V_1 = 82$ volts<br>$V_2 = -41$ volts<br>$t_1 = 40$ sec.<br>$t_2 = 56$ sec.<br>H3 gel box | EXAMPLE VI<br>$V_1 = 82$ volts<br>$V_2 = -41$ volts<br>$t_1 = 60$ sec.<br>$t_2 = 84$ sec.<br>H3 gel box |
| 6.6 kbp | 92 mm | 97 mm | 96 mm |

TABLE I-continued

| DNA Size | | | |
|---|---|---|---|
| 9.4 kbp | 86 mm | 93 mm | 91 mm |
| 14.0 kbp | — | — | — |
| 23.1 kbp | 72 mm | 78 mm | 77 mm |
| 41.7 kbp | 70 mm | 74 mm | 74 mm |
| 71 kbp | 66 mm | 70 mm | 72 mm |
| 125 kbp | 61 mm | 66 mm | 68 mm |
| 170 kbp | 54 mm | 61 mm | 65 mm |
| 230 kbp | 45 mm | 55 mm | 62 mm |
| 360 kbp | 22 mm | 42 mm | 56 mm |
| 460 kbp | 6 mm | 20 mm | 51 mm |
| 540 kbp | 4 mm | — | 29 mm |
| 700 kbp | 4 mm | — | 22 mm |
| 1600 kbp | 4 mm | 7 mm | — |
| 2400 kbp | 4 mm | 7 mm | — |
| 3000 kbp | 4 mm | 7 mm | 14 mm |
| 4500 kbp | 4 mm | 7 mm | 14 mm |
| 6000 kbp | 4 mm | 7 mm | 14 mm |

| DNA Size (in kbp) | EXAMPLE VII $V_1 = 82$ volts $V_2 = -41$ volts $t_1 = 250$ sec. $t_2 = 350$ sec. H3 gel box | EXAMPLE VIII $V_1 = 82$ volts $V_2 = -41$ volts $t_1 = 160$ sec. $t_2 = 224$ sec. H3 gel box | EXAMPLE IX $V_1 = 82$ volts $V_2 = -41$ volts $t_1 = 1280$ sec. $t_2 = 1792$ sec. H3 gel box |
|---|---|---|---|
| 6.6 kbp | 90 mm | 52 mm | 47 mm |
| 9.4 kbp | 86 mm | 47 mm | 42 mm |
| 14.0 kbp | — | 46 mm | 41 mm |
| 23.1 kbp | 73 mm | 42 mm | 38 mm |
| 41.7 kbp | 70 mm | 40 mm | 36 mm |
| 71 kbp | 68 mm | 37 mm | 34 mm |
| 125 kbp | 65 mm | 35 mm | 32 mm |
| 170 kbp | 63 mm | 33 mm | 31 mm |
| 230 kbp | 60 mm | 31 mm | 30 mm |
| 360 kbp | 58 mm | 28 mm | — |
| 460 kbp | 56 mm | 26 mm | — |
| 540 kbp | 52 mm | 25 mm | — |
| 700 kbp | 50 mm | 19 mm | 26 mm |
| 1600 kbp | 50 mm | 1 mm | 24 mm |
| 2400 kbp | 40 mm | 1 mm | 24 mm |
| 3000 kbp | 17 mm | 2 mm | 24 mm |
| 4500 kbp | 12 mm | 2 mm | 7 mm |
| 6000 kbp | 3 mm | 2 mm | 2 mm |

Results of Example I to IX. The first column, DNA Size (in kbp) provides the molecular size of the DNA molecules selected. The other 9 columns provide the distance migrated (location) in millimeters for each of these DNA molecules. $V_1$ and $V_2$ refer to the voltages applied between the two electrodes in the electrophoresis device indicated, H3 or H1, and $t_1$ and $t_2$ refer to the pulse duration time. The stars ** indicate the range of molecular sizes for the Examples which provided the highest resolution. Thus, the highest resolution for Example I was between 41.7 and 71 kbp.

TABLE II

| PULSE CONDITIONS: $V_1 = 82$ Volts $V_2 = -41$ Volts H3 box | PERCENT OF THE DURATION OF THE EXAMPLE WHERE THIS PULSE WAS USED |
|---|---|
| $t_1 = 2$ sec $t_2 = 2.8$ sec | 22.6% |
| $t_1 = 5$ sec $t_2 = 7$ sec | 0.646% |
| $t_1 = 10$ sec $t_2 = 14$ sec | 13.15% |
| $t_1 = 30$ sec | 9.48% |

TABLE II-continued

| PULSE CONDITIONS: $V_1 = 82$ Volts $V_2 = -41$ Volts H3 box | PERCENT OF THE DURATION OF THE EXAMPLE WHERE THIS PULSE WAS USED |
|---|---|
| $t_2 = 42$ sec $t_1 = 50$ sec $t_2 = 70$ sec | 18.0% |
| $t_1 = 160$ sec $t_2 = 224$ sec | 36.0% |

TABLE III

| DNA Size (in kbp) | $V_1 = 82$ volts $V_2 = -41$ volts $t_1 = 50$ sec. $t_2 = 70$ sec. H3 gel box | $V_1 = 82$ volts $V_2 = -41$ volts $t_1 = 160$ sec. $t_2 = 224$ sec. H3 gel box |
|---|---|---|
| 23.1 kbp | 78 mm | 79 mm |
| 41.7 kbp | 74 mm | 76 mm |
| 71 kbp | 70 mm | 74 mm |
| 125 kbp | 66 mm | 72 mm |
| 170 kbp | 62 mm | 68 mm |
| 230 kbp | 58 mm | 67 mm |
| 360 kbp | 51 mm | 64 mm |
| 460 kbp | 34 mm | 63 mm |
| 540 kbp | 14 mm | 61 mm |
| 700 kbp | — | 58 mm |
| 1600 kbp | 9 mm | 50 mm |
| 2400 kbp | 9 mm | 11 mm |

APPENDIX I

THE COMPUTER ALGORITHM PROGRAM USED IN EXAMPLE X

1. Read data from a user selected data file:
   R rows (one for each different DNA fragment size),
   C column (one for each set of experimental data).
2. User chooses subset of N rows and N columns to work on (this gives a N×N matrix of data).
3. User chooses the values of N−1 desired final relative displacements (these are the relative separation distances between the N molecules).
4. User chooses the displacement origin (this provides a measure of the desired absolute displacements).
5. Invert matrix to obtain the vector of the N time durations for each of the N selected sets of experimental conditions. The LU Decomposition algorithm described in section 2.3 of *Numerical Recipes*, by W. H. Press, B. P. Flannery, S. A. Teukotsky and W. T. Vetterling, Cambridge University Press, Cambridge, 1986, hereby incorporated by reference, was selected.
6. Are the results acceptable? If yes, selected is complete. If no, go back to step 2 and repeat.

APPENDIX II

INTRODUCTION

To provide flexibility for pulsed field gel electrophoresis of the present invention, a system has been developed and utilized that provides programmable control of the fields applied to the gels while monitoring some of the conditions induced by these applied fields. The system consists of a microprocessor running the MS-DOS operating system for basic processor control parameters and a specially written program, GELPHOR, see the block diagram that follows, to generate the field control functions and record some of the operating conditions.

HARDWARE

The machine used was a generic version of the IBM-XT configured with 640Kb memory, floppy disk drive, 20Mb fixed disk, high resolution graphic display card, serial and parallel ports, clock, high resolution monochrome monitor and a dot matrix printer.

The hardware utilizes A/D and D/A boards supplied by Strawberry Tree Inc. to implement the control and monitoring process. Probes are supplied to monitor the temperature and field in the solution and a low value resistor is included in the circuit of the gel controller to monitor current flow.

The controller was the power supply for the gel trays and the signal conditioner for the measurements. The unit is capable of supplying power to four trays, that is four electrophoresis devices, however, for Example XI the H3 electrophoresis gel device (Gel Experiment 1) or one tray was selected with a maximum current of 0.1 Amps at 90 volts (direct current) in both the positive and negative directions. Signals are received from gel probes, and translated to suitable values for returning to the analog to digital convertor board. This board is capable of monitoring sixteen channels to an accuracy of twelve binary bits (1 part in 4096). The Figure Layout that follows illustrates schematically the equipment set up to control the four trays.

The probes are comprised of a plexiglass housing containing two platinum electrodes to measure the voltage drop in the electrolyte and a glass encased platinum resistance element to monitor the temperature rise under the chosen pulse conditions. The method used to insert the probe into the gel was to drill a 5/8 inch diameter hole in the gel box cover at the extremity of the gel closest to the negative (black) voltage terminal.

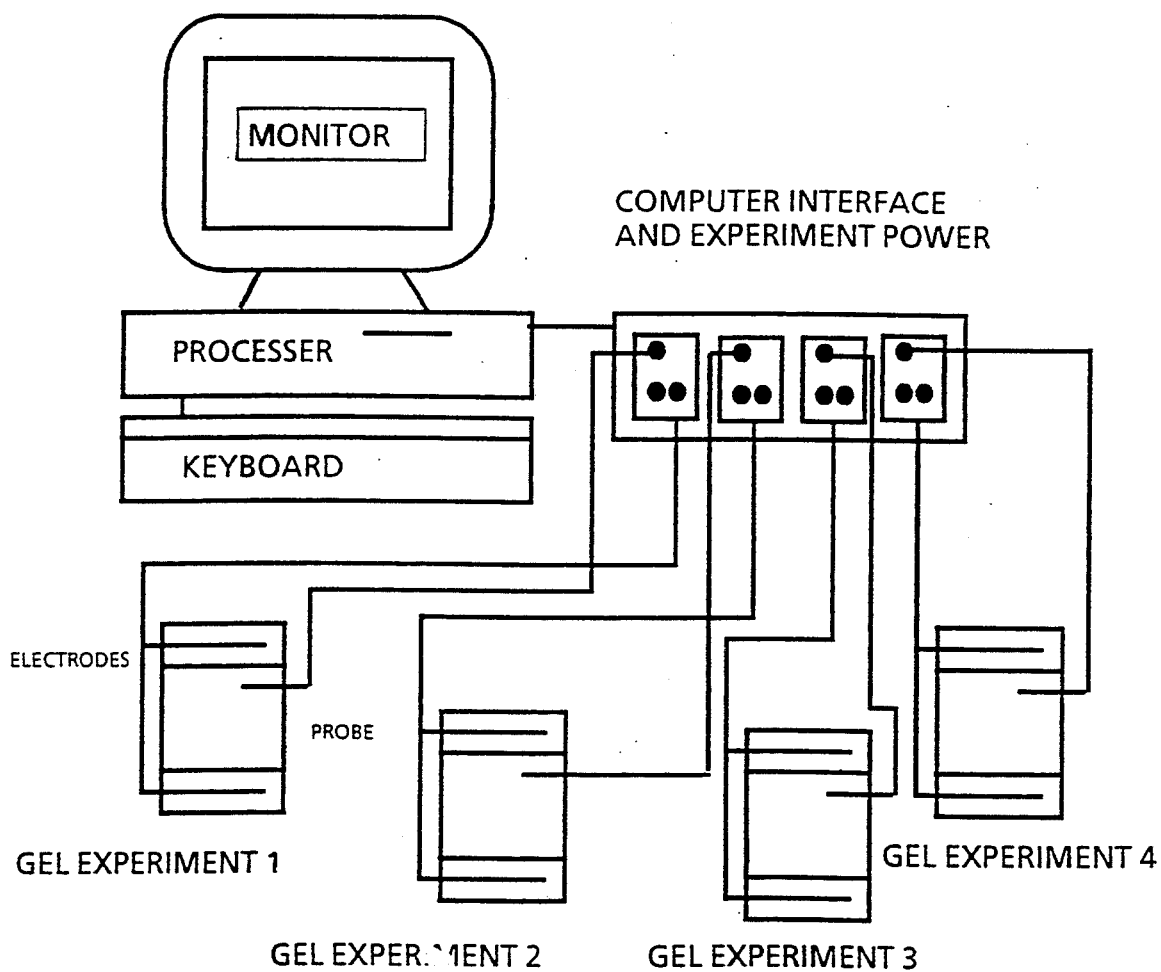

FIGURE - LAYOUT OF GEL ELECTROPHORESIS CONTROL SYSTEM

SOFTWARE

Program Gelphor

The methods and displays of the Program Gelphor are partly based on a set of functional specifications. This program allows one to run different experiments on four separate trays simultaneously. Setting up each experiment was a simple process in which the program itself will guide the user through. First, we define a PULSE and how it is described to the program.

A pulse is a periodic sequence of voltages defined over one cycle as a series of duration times (in seconds) and the voltage to be applied to the tray electrodes for that duration. For example, if it is desired to apply a simple square wave alternating between +50 volts and -50 volts every 30 seconds (for Example XI, $V_1$ was 82 volts, and $V_2$ was -26 volts; and the times were as recited in Example XI), it would be specified as the list 30 50 30 -50. The first 30 is the duration time for which 50 volts is to be applied, the second 30 the duration for which -50 volts is to be applied. The program will repeat this sequence over and over for a length of time specified as indicated herein. Both time and voltage can be decimal numbers. Each number must be separated from the others by one or more spaces. There is no specific limit to the number of duration-voltage pairs one can select to specify a pulse (subject to the finite size of computer memory), but pulses with hundreds of duration-voltage pairs are feasible. A saw-tooth pulse with the voltage changing every tenth of a second could be described as follows: 0.1 0 0.1 5 0.1 10 0.1 15 0.1 20. This is interpreted as a tenth of a second at 0 volts, a tenth at 5 volts, a tenth at 10 volts and so on. These two examples illustrate all the duration times being the same, however, they can be of any value from 0.01 second up, for example up to about one year.

Program Gelphor provides up to 10 distinct pulses to each of the electrophoresis trays in a timed sequence that the user describes.

Individual pulse descriptions are stored on named files which contain lists of time voltage pairs as text characters in exactly the format described in the previous paragraph. Making such a ..'e manually is simple (program Gelphor contains facilities to guide the user through the process), however, complex pulse shapes, which were not utilized for Example XI can be generated by another program based on theoretical predictions. Pulse files can have any name, but must conform to the Disk Operating System (DOS) format, which is a name up to 8 characters long followed by a period and then a 3 character extension. Gelphor will only recognize files with the extension PLS (short for pulse), thus one can, for example, identify the square pulse as indicated herein, SQUARE.PLS, and the saw-tooth SAW.PLS. A representation of a pulse profile is illustrated in the following Figure. When one creates pulses through the programs facilities, it is not necessary to type in this extension, it will be added automatically when the files are stored on disc.

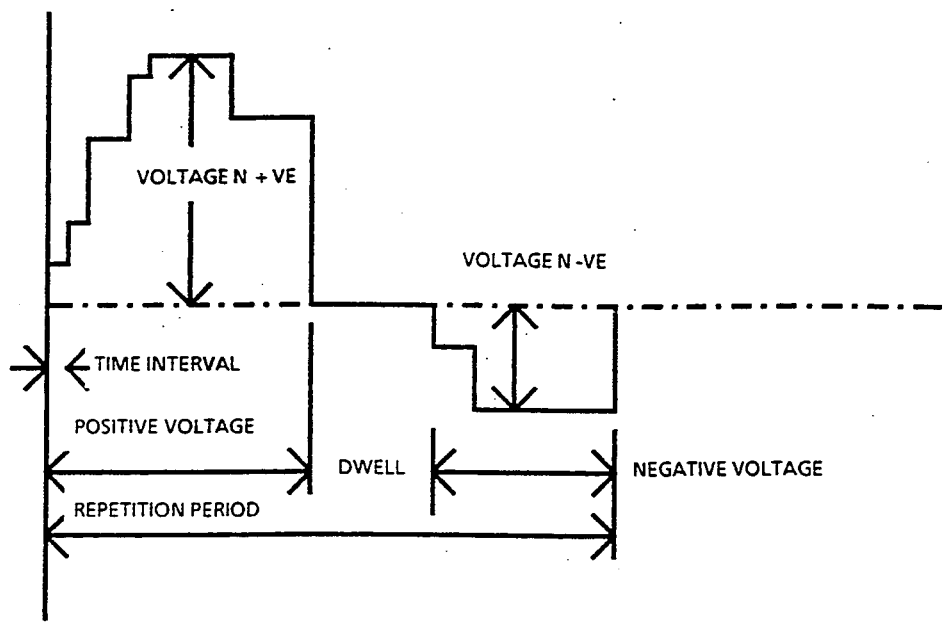

FIGURE - PULSE PROFILE

When program Gelphor is started, the user is presented with a screen (which will be referred to as the top level screen) that has a title at the top and four rectangular boxes labeled Tray 1 through Tray 4 (only one tray, or H3 device used in Example XI). Inside each box there is some information about the experiment running on each tray. When the system is initially turned on, each o. these boxes indicate that its tray is inactive, and invite the user to press a function key to start it up. The function keys F1 through F10 are on the left-hand side of the keyboard. When the keys F1 - F4 are pressed to initiate an experiment, Gelphor looks to see if there is a floppy disk in drive 'A:', and then if there are any files ending with .PLS on the disk. It then looks for more .PLS files on the hard disk (drive C:) on a directory whose path is C:\DNA\PULSE. If no .PLS files are found, the user is asked whether it is desired to proceed to making one. The default answer to this question is Y for yes. If one presses N and the 'enter' key, the program will simply return to the top level screen. If it is decided to proceed in making a pulse file, the user is presented with a series of screens which function as a guide through the process.

When Gelphor locates one or more existing pulse files, up to the first 48 it finds will be displayed on the left-hand side of a screen. The user is then invited to select up to 10 to be run on the experiment. The selection process involves using the up and down arrow keys to highlight the pulse(s) wanted and pressing the space bar to copy the highlighted name to the selection box on the right of the screen. At any time in this process, pressing the M key will invoke the keyboard pulse entry routine and allow the user to create another file to be inserted in the selection box. If an error is made during pulse selection, pressing R restarts the process. Pressing F ends the selection process and moves on to a scheduling screen.

Gelphor permits the user to choose between setting the starting times of each of the pulses, option 1, or specifying the duration time, option 2. The third option permits the user to rearrange the order in which to select the schedule of pulses. The screens which appear with each of these options are self explanatory. Only one pulse sequence was utilized in Example XI Next, the user is asked to specify a name for the experiment which Gelphor uses to maintain a logging file of important information, and finally the user is asked to confirm that it is desired to proceed with the experiment.

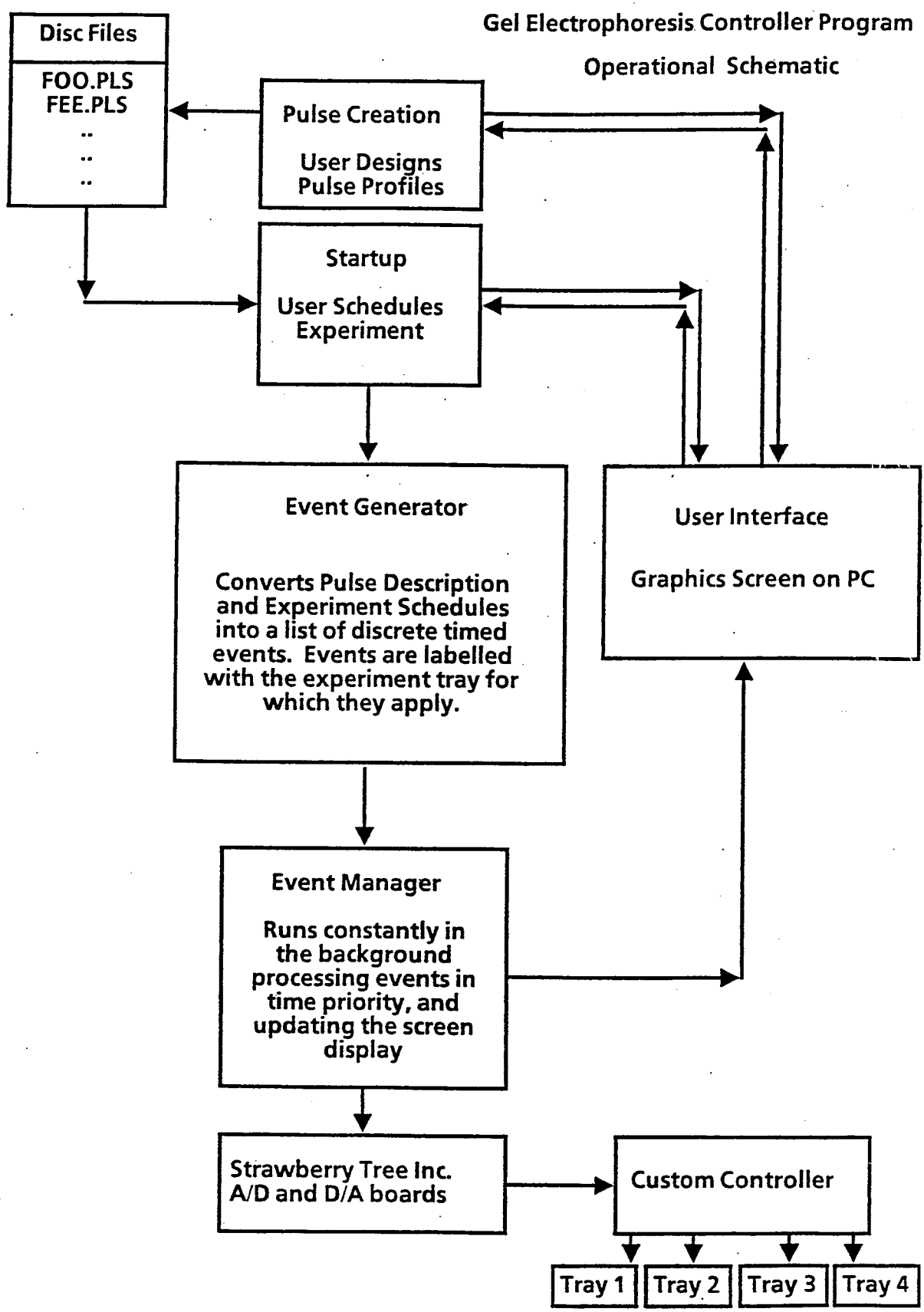

What is claimed is:

1. A process for the electrophoretic separation of charged macromolecules which comprises applying to said macromolecules a periodic sequence of pulses with each period comprising a multiplicity of electric field pulses of negative polarities and positive polarities, wherein the negative polarity pulses are applied for a longer total time duration than the positive polarity pulses within each period, and the average intensity of the negative polarity pulses is less than the average intensity of the positive polarity pulses.

2. A process in accordance with claim 1 wherein substantially all of the negative polarity pulses are of lower intensities than the positive polarity pulses.

3. A process in accordance with claim 1 wherein the separation is accomplished in an electrophoresis device.

4. A process in accordance with claim 1 wherein the macromolecules are contained in a gel.

5. A process in accordance with claim 4 wherein the gel is Agarose NA.

6. A process in accordance with claim 1 wherein the macromolecules are comprised of DNA.

7. A process in accordance with claim 1 wherein the electric field pulses are applied for a total of from about 1 to about 10 days.

8. A process in accordance with claim 1 wherein the electric field pulses are applied for a total of about 3 days.

9. A process in accordance with claim 1 wherein the positive polarity pulses last from about 0.1 to about 10,000 seconds for each pulse.

10. A process in accordance with claim 1 wherein the positive polarity voltages pulses within a period are applied with a value of more than 0 to about a positive 10 volts per centimeter for each pulse.

11. A process in accordance with claim 1 wherein the negative polarity pulses last from about 0.1 to about 10,000 seconds for each pulse.

12. A process in accordance with claim 1 wherein the negative polarity pulses within a period are applied with a value of less than 0 to about a negative 10 volts per centimeter for each pulse.

13. A process in accordance with claim 1 wherein each period comprises time intervals of zero-field intensity.

14. A process in accordance with claim 1 wherein at least one of the negative polarity pulses is of a lower value than any of the positive polarity pulses.

15. A process in accordance with claim 1 wherein a majority of the negative polarity pulses are of lower intensities than the positive polarity pulses.

16. A process in accordance with claim 1 wherein an average field intensity is computed as being the sum of the products of the pulse intensities multiplied by the pulse durations, divided by the sum of the pulse durations, and wherein nonzero intensity pulses are excluded.

17. A process for the electrophoretic separation of charged macromolecules which comprises applying to said macromolecules a periodic sequence of pulses with each period comprising a multiplicity of electric field pulses of negative polarities and positive polarities wherein the negative polarity pulses are applied for a longer time duration than the positive polarity pulses, and the average intensity of the negative polarity pulses is less than the average intensity of the positive polarity pulses and wherein zero integrated field electrophoresis is applied whereby the net integrated value of the electric field pulses during one complete period is zero.

18. A process for the electrophoretic separation of charged macromolecules which comprises applying to said macromolecules a periodic sequence of pulses with each period comprising a multiplicity of electric field pulses of negative polarities and positive polarities wherein the negative polarity pulses are applied for a longer time duration than the positive polarity pulses, and the average intensity of the negative polarity pulses is less than the average intensity of the positive polarity pulses and wherein field pulse durations, and field intensities are changed during the process.

19. A process for the separation of charged macromolecules which comprises repeatedly applying to said macromolecules contained in an electrophoresis device a periodic sequence of pulses with each period comprising pulses of a first electric field and pulses of a second electric field, and wherein the fields are of opposite polarity and along a single dimension; the second field is of lower intensity than the first field; and the second field is applied for a longer duration than the first field for each period.

20. A process in accordance with claim 19 wherein the first electric field is applied for about 0.1 to about 10,000 seconds for each period.

21. A process in accordance with claim 19 wherein the second electric field is applied for about 0.1 to about 10,000 seconds for each period.

22. A process in accordance with claim 19 wherein the first electric field is of a positive polarity.

23. A process in accordance with claim 19 wherein the first electric field is of an intensity of from about 0.5 to about 10 volts/centimeter.

24. A process in accordance with claim 19 wherein the second electric field is of a negative polarity.

25. A process in accordance with claim 19 wherein the second electric field is of an intensity of from about 0.2 to about 5 volts/centimeter.

26. A process for the separation of charged macromolecules which comprises repeatedly applying to said macromolecules contained in an electrophoresis device a periodic sequence of pulses with each period comprising pulses of a first electric field and pulses of a second electric field and wherein the fields are of opposite polarity and along a single dimension; the second field is of lower intensity than the first field; and the second field is applied for a longer duration than the first field for each period and wherein zero integrated field electrophoresis is applied whereby the net integrated value of the first and second electric fields during one complete period is about zero.

27. A process in accordance with claim 26 wherein the macromolecules are contained in a gel.

28. A process in accordance with claim 27 wherein the gel is Agarose NA.

29. A process in accordance with claim 28 wherein the concentration of agarose in the gel is between about 0.2 and about 2 percent.

* * * * *